(12) United States Patent
Zhang et al.

(10) Patent No.: US 8,140,156 B2
(45) Date of Patent: Mar. 20, 2012

(54) HEART SOUND SENSING TO REDUCE INAPPROPRIATE TACHYARRHYTHMIA THERAPY

(75) Inventors: Xusheng Zhang, Shoreview, MN (US); David A. Anderson, Stanchfield, MN (US); Jeffrey M. Huston, Minneapolis, MN (US); Jeffrey M. Gillberg, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 382 days.

(21) Appl. No.: 12/495,204

(22) Filed: Jun. 30, 2009

(65) Prior Publication Data

US 2010/0331903 A1 Dec. 30, 2010

(51) Int. Cl.
*A61N 1/00* (2006.01)
(52) U.S. Cl. .......................................... 607/17
(58) Field of Classification Search .................. 600/508, 600/218, 528; 607/4, 9, 17
See application file for complete search history.

(56) References Cited

U.S. PATENT DOCUMENTS

| | | | |
|---|---|---|---|
| 4,374,382 A | 2/1983 | Markowitz | |
| 4,763,646 A | 8/1988 | Lekholm | |
| 5,117,824 A | 6/1992 | Keimel et al. | |
| 5,545,186 A | 8/1996 | Olson et al. | |
| 5,755,736 A | 5/1998 | Gillberg et al. | |
| 6,393,316 B1 | 5/2002 | Gillberg et al. | |
| 6,477,406 B1 | 11/2002 | Turcott | |
| 6,643,548 B1 | 11/2003 | Mai et al. | |
| 7,174,203 B2 | 2/2007 | Arand et al. | |
| 7,209,786 B2 | 4/2007 | Brockway et al. | |
| 7,218,966 B2 | 5/2007 | Haefner | |
| 2003/0060723 A1 | 3/2003 | Joo et al. | |
| 2004/0127792 A1 | 7/2004 | Siejko et al. | |
| 2005/0010257 A1 | 1/2005 | Lincoln et al. | |
| 2006/0241702 A1 | 10/2006 | Gillberg | |
| 2006/0282000 A1 | 12/2006 | Zhang et al. | |
| 2007/0142866 A1* | 6/2007 | Li et al. ............................ | 607/17 |
| 2007/0149890 A1 | 6/2007 | Li et al. | |
| 2007/0239218 A1 | 10/2007 | Carlson et al. | |
| 2008/0177191 A1 | 7/2008 | Patangay et al. | |

OTHER PUBLICATIONS

U.S. Appl. No. 12/357,868, filed Jan. 22, 2009, entitled "A Blurred Template Approach for Arrhythmia Detection," to Zhang et al.
Response to Written Opinion for PCT/US2010/030268 filed Apr. 27, 2011, 13 pp.
International Preliminary Report on Patentability from international application No. PCT/US2010/030268, dated May 30, 2011, 11 pp.
Written Opinion and Search Report from PCT/US2010/030268, dated Jun. 21, 2010, (13 pp.).

* cited by examiner

*Primary Examiner* — George Manuel
*Assistant Examiner* — Robert Wieland
(74) *Attorney, Agent, or Firm* — Michael C. Soldner

(57) ABSTRACT

Techniques for detecting heart sounds to reduce inappropriate tachyarrhythmia therapy are described. In some examples, a medical device determines that a cardiac rhythm of the patient is treatable with a therapy, such as a defibrillation pulse, based on a cardiac electrogram (EGM). The medical device analyzes detected heart sounds, and withholds or allows the therapy based on the analysis of the heart sounds.

33 Claims, 15 Drawing Sheets

HEART SOUND SENSING TO REDUCE INAPPROPRIATE TACHYARRHYTHMIA THERAPY

TECHNICAL FIELD

This disclosure relates to medical devices and, more particularly, to medical devices that deliver therapy to terminate tachyarrhythmia.

BACKGROUND

Medical devices, such as implantable cardioverter-defibrillators, provide therapeutic electrical stimulation to the heart in order to terminate tachyarrhythmia, such as tachycardia or fibrillation. The electrical stimulation may include signals such as pulses or shocks for pacing, cardioversion or defibrillation. In some cases, the medical device may sense intrinsic depolarizations of the heart, detect tachyarrhythmia based on the intrinsic depolarizations, and control delivery of electrical stimulation to the heart if tachyarrhythmia is detected based on the intrinsic depolarizations.

Medical devices sense signals and deliver therapeutic stimulation via electrodes. Implantable pacemakers, cardioverters, defibrillators, or pacemaker-cardioverter-defibrillators are typically coupled to one or more intracardiac leads that carry electrodes for cardiac sensing and delivery of therapeutic stimulation. The signals sensed via the electrodes may be referred to as a cardiac electrogram (EGM), e.g., an electrocardiogram (ECG), and may include the depolarizations and other intrinsic electrical activity of the heart.

In some cases, a medical device delivers therapeutic electrical stimulation, such as a defibrillation pulse, when the stimulation is not required. Delivery of such inappropriate therapy by a medical device is often due to misinterpretation of the cardiac electrogram as indicating a rapid or unstable ventricular tachycardia or ventricular fibrillation. In some cases, the medical device detects a rapid ventricular tachycardia or ventricular fibrillation when the cardiac rhythm is in fact stable, or otherwise not requiring a defibrillation pulse, such as sinus tachycardia (ST), supraventricular tachycardia (SVT), or rapid atrial tachycardia/atrial fibrillation (AT)/(AF) conducted to the ventricles, or a hemodynamically stable ventricular tachycardia (VT). In some cases, the medical device misinterprets T-waves in the cardiac EGM as R-waves, which is referred to as T-wave over-sensing (TWOS), and may cause the medical device to interpret the cardiac rhythm as having a higher ventricular rate than the actual rate. In some cases, the medical device over-senses R-waves due to nonphysiological or non-cardiac signals in the cardiac EGM, which may be the result of electromagnetic interference (EMI), EGM clipping, lead fracture, or muscle noise, as examples. Implantable medical devices that detect the cardiac EGM via implantable medical leads may be susceptible to oversensing due to nonphysiological or non-cardiac signals in the cardiac EGM.

SUMMARY

Techniques for detecting heart sounds to reduce inappropriate tachyarrhythmia therapy are described. Heart sound sensing may not be susceptible to the same types of oversensing and misinterpretation as cardiac EGM sensing. In some examples, a therapy scheduled to be delivered based on an analysis of the EGM may be allowed or withheld based on heart sound sensing. In this manner, heart sound sensing may allow a medical device to avoid delivering inappropriate tachyarrhythmia therapy, such as delivery of one or more defibrillation pulses in the presence of a stable rhythm or oversensing.

In some examples, a medical device processes a heart sound sensor signal to generate an envelope signal, and detects heart sounds within the envelope signal. In some examples, the medical device detects the heart sounds using an adaptively decaying detection threshold. The medical device may determine the decaying detection threshold based on a running average of detected heart sound peaks, a running average of the envelope signal amplitude for heart sound intervals, and a mean of the heart sound intervals.

In some examples, the medical device analyzes features of the detected heart sounds, and classifies the detected heart sounds as either normal or abnormal based on the features of the detected heart sounds. In some examples, the medical device analyzes the envelope signal, a filtered version of the heart sound signal, or both, within a window around a detected heart sound to determine the features of the detected heart sounds. In some examples, the medical device confirms that a cardiac rhythm is treatable when one or more heart sounds are classified as abnormal, or withholds therapy when one or more heart sounds are classified as normal.

As used herein, the term heart sound refers to a feature of a heart sound signal, such as the S1, S2, S3, or S4 heart sounds. There may be multiple heart sounds, e.g., each of an S1, S2, S3 and S4 heart sound, for any given cardiac cycle or heart beat. In some examples, the medical device classifies a heart beat or cardiac cycle as normal or abnormal based on the classifications for one or more heart sounds detected during the heart beat or cardiac cycle. In such examples, the medical device may confirm that a cardiac rhythm is treatable when one or more heart beats are classified as abnormal, or withhold therapy when one or more heart beats are classified as normal In some examples, the medical device delivers pacing pulses, such as anti-tachycardia pacing (ATP) pulses, and analyzes one or more features of the heart sound signal, or heart sounds identified within the heart sound signal, during the delivery of pacing pulses. The response of the heart sound signal to the pacing may indicate whether the pacing, e.g., ATP, is effective, and whether the heart is experiencing fibrillation or another tachyarrhythmia. In some examples, the medical device may monitor for normal heart sounds in response to delivery of the pacing pulses. In some examples, if the medical device determines that ATP therapy is not effective and/or the heart is in fibrillation, the medical device delivers further antitachyarrhythmia therapy, such as cardioversion or defibrillation therapy.

In one example, a method comprises determining that a cardiac rhythm of a heart of a patient is treatable by delivery of an antitachyarrhythmia therapy from a medical device to the patient based on an analysis of electrical activity of the heart of the patient, receiving a heart sound signal from a heart sound sensor, the heart sound signal representing sounds generated by the heart and blood flow of the patient, and detecting a plurality of heart sounds within the heart sound signal. The method further comprises classifying each of the detected heart sounds as one of a first classification or a second classification based on one or more features of the detected heart sounds, and selectively delivering or withholding the antitachyarrhythmia therapy based on the classifications of the detected heart sounds.

In another example, a system comprises a heart sound sensor that generates a heart sound signal representative of sounds of a heart of a patient, a medical device, a processor that determines that a cardiac rhythm of the heart is treatable by delivery of an antitachyarrhythmia therapy from the medical device to the patient based on an analysis of electrical activity of the heart of the patient, and a heart sound analyzer. The heart sound analyzer receives the heart sound signal from the heart sound sensor, detects a plurality of heart sounds within the heart sound signal, and classifies each of the detected heart sounds as one of a first classification or a second classification based on one or more features of the detected heart sounds. The processor selectively controls the medical device to deliver or withhold the antitachyarrhythmia therapy based on the classifications of the detected heart sounds.

In another example, a system comprises means for determining that a cardiac rhythm of a heart of a patient is treatable by delivery of an antitachyarrhythmia therapy from a medical device to the patient based on an analysis of electrical activity of the heart of the patient, means for receiving a heart sound signal from a heart sound sensor, the heart sound signal representing sounds of the heart of the patient, means for detecting a plurality of heart sounds within the heart sound signal, means for classifying each of the detected heart sounds as one of a first classification or a second classification based on one or more features of the detected heart sounds, and means for selectively delivering or withholding the antitachyarrhythmia therapy based on the classifications of the detected heart sounds.

In other examples, a computer-readable medium comprises instructions executable by a processor that cause the processor to perform any of the methods described herein.

DETAILED DESCRIPTION

The techniques described in this disclosure allow a medical device to detect heart sounds to reduce inappropriate delivery of tachyarrhythmia therapy. Detecting heart sounds may reduce inappropriate delivery of therapy because heart sounds provide complementary beat-by-beat information that can be used to corroborate EGM based decisions. In addition, heart sounds are not susceptible to the same noise sources or other misinterpretation issues as EGMs. For example, the heart sound sensor may more immune to noise that negatively effects EGMs, such as EMI and muscle noise.

In general, heart sounds are associated with mechanical vibrations of a patient's heart and the flow of blood through the heart and, thus, are highly correlated with pressure gradients across heart valves and blood pressure. Heart sounds are not only due to vibrations of and pressure within the heart, but may be due to the whole cardiohemic system, e.g., blood, heart, great arteries, etc. Heart sounds recur with each cardiac cycle and are separated and classified according to the activity associated with the vibration. The first heart sound is referred to as "S1," and can be thought of as the vibrational sound made by the heart during closure of the atrioventricular (AV) valves, i.e., the mitral valve and tricuspid valve. The second heart sound is referred to as "S2," and results from the closure of the semilunar valves, i.e., the pulmonary and aortic valves. The S2 heart sound can be thought of as marking the beginning of diastole. The third and fourth heart sounds are referred to as "S3" and "S4," respectively, and can be conceptualized as related to filling of the ventricles during diastole. S3 is due to rapid filling of the ventricles and can occur when the ventricular wall is not relaxed when a large volume of blood flows into the ventricle from the atria. S4 is caused by blood rapidly filling into the ventricles from the atria due to atrial contraction.

The described techniques may enhance specificity with minimal impact on sensitivity. In particular, the described techniques may successfully withhold an incorrect EGM based decision that a rhythm is treatable with a therapy, such as defibrillation, and not withhold a correct EGM based decision that a rhythm is a treatable ventricular tachycardia (VT) or ventricular fibrillation (VF).

Additionally, a heart sound sensor, such as a piezoelectric sensor or other acoustic sensor, may be easy to implement with an implantable medical device (IMD), e.g., on a lead or within a housing of the IMD. Enclosing the sensor within the housing of the IMD may provide additional protection for the sensor.

Figure 1:
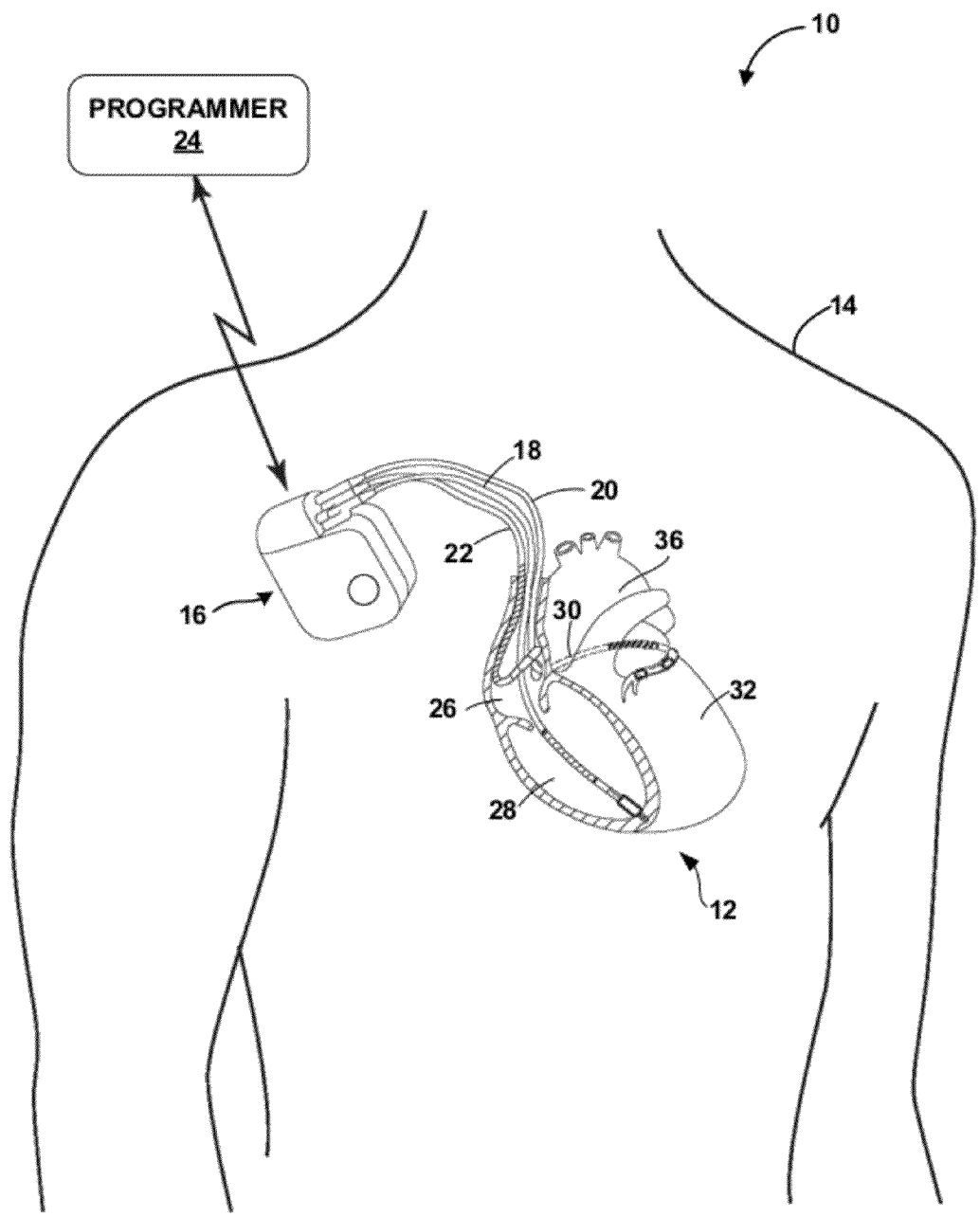
FIG. 1 is a conceptual diagram illustrating an example system that detects heart sounds to reduce inappropriate delivery of tachyarrhythmia therapy.

FIG. 1 is a conceptual diagram illustrating an example system 10 that detects heart sounds to reduce inappropriate delivery of tachyarrhythmia therapy to patient 14. In particular, system 10 determines whether a cardiac rhythm of patient 14 is treatable based, at least in part, on detected heart sound sounds of the patient. In some examples, system 10 may first determine whether a cardiac rhythm is treatable or non-treatable based on a cardiac EGM. If system 10 determines the rhythm is treatable based on the EGM, system 10 may attempt to confirm the determination based on monitored heart sounds of patient 14. For example, based on detected heart sounds, system 10 may confirm the indication and deliver the therapy to patient 14, or deny the indication and withhold the therapy. Determining whether a rhythm is treatable or non-treatable based on an EGM and heart sounds may reduce inappropriate delivery of tachyarrhythmia therapy to patient 14.

System 10 includes implantable medical device (IMD) 16, which is connected to leads 18, 20, and 22, and communicatively coupled to a programmer 24. IMD 16 senses electrical signals attendant to the depolarization and repolarization of heart 12, e.g., a cardiac EGM, via electrodes on one or more of leads 18, 20 and 22 or a housing of IMD 16. IMD 16 also delivers therapy in the form of electrical signals to heart 12 via electrodes located on one or more leads 18, 20, and 22 or a housing of IMD 16, such pacing, cardioversion and/or defibrillation pulses. IMD 16 also includes, or is coupled to via one or more of leads 18, 20 and 22, one or more heart sound sensors (not shown in FIG. 1). IMD may similarly include or be coupled to other sensors, such as one or more accelerometers, for detecting other physiological parameters of patient 14, such as activity or posture.

In some examples, programmer 24 takes the form of a handheld computing device, computer workstation, or networked computing device that includes a user interface for presenting information to and receiving input from a user. A user, such as a physician, technician, surgeon, electrophysiologist, or other clinician, may interact with programmer 24 to communicate with IMD 16. For example, the user may interact with programmer 24 to retrieve physiological or diagnostic information from IMD 16. A user may also interact with programmer 24 to program IMD 16, e.g., select values for operational parameters of the IMD.

IMD 16 and programmer 24 may communicate via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 16 implant site in order to improve the quality or security of communication between IMD 16 and programmer 24. In other examples, programmer 24 may be located remotely from IMD 16, and communicate with IMD 16 via a network.

As will be described in greater detail, IMD 16 may deliver therapeutic stimulation or "therapy" to patient 14 for terminating a tachyarrhythmia of heart 12 based, at least in part, on heart sounds. Examples of tachyarrhythmias include ventricular tachycardia and ventricular fibrillation. Examples of therapeutic stimulation to terminate tachyarrhythmia include pacing, e.g., anti-tachycardia pacing (ATP), cardioversion and defibrillation.

The techniques for reducing inappropriate therapy based on heart sounds are primarily described herein as being performed by IMD 16, e.g., by a processor of IMD 16. In other examples some or all of the functions ascribed to IMD 16 or a processor thereof may be performed by one or more other devices, such as programmer 24, or a processor thereof. For example, programmer 24 may process heart sound and/or EGM signals received from IMD 16 to determine whether a therapy should be delivered to terminate a tachyarrhythmia, and control whether IMD 16 delivers the therapy. Furthermore, although described herein with respect to an IMD, in other examples, the techniques described herein may be performed by or implemented in an external medical device, which may be coupled to a patient via percutaneous or transcutaneous leads.

Figure 2:
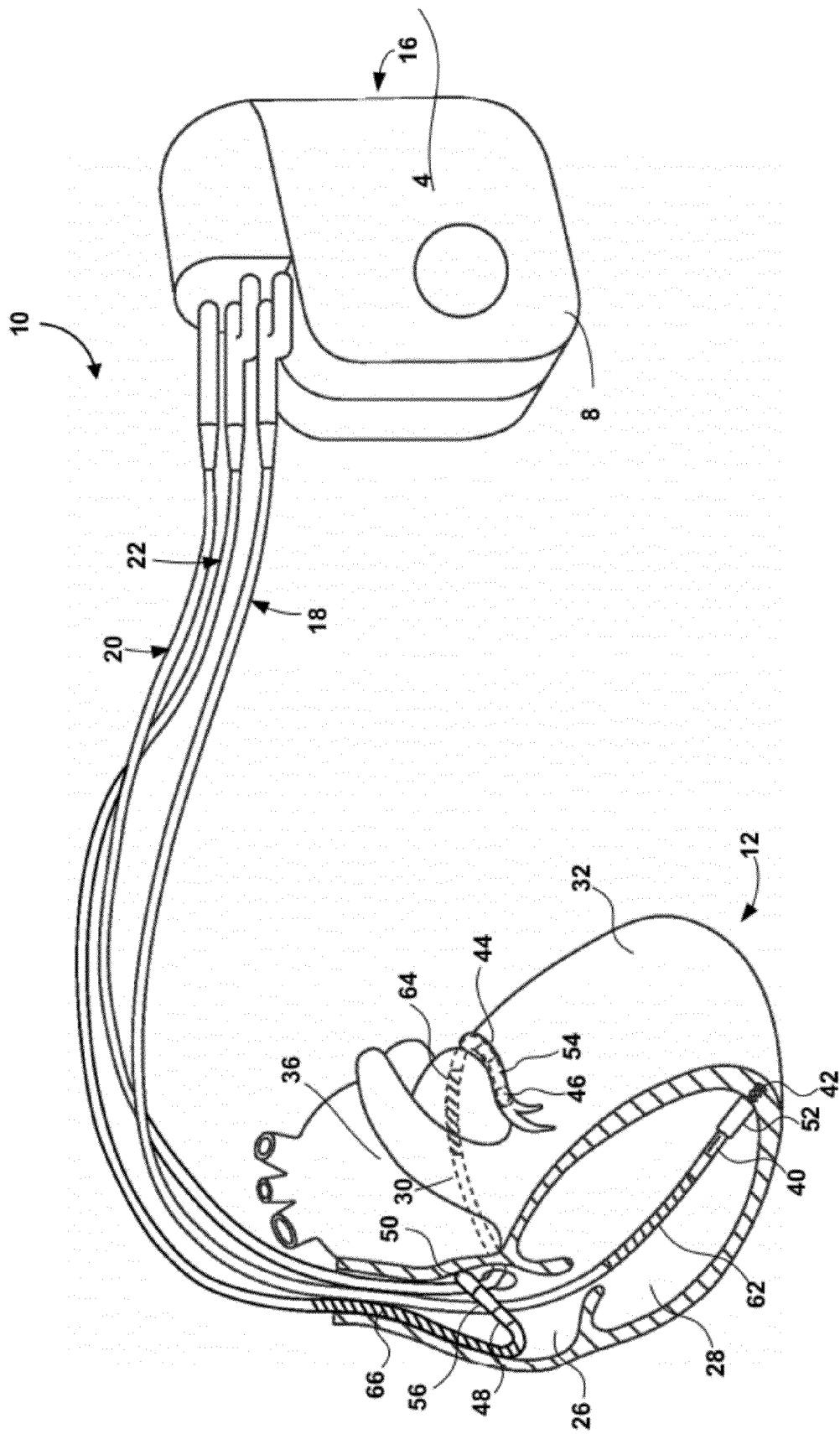
FIG. 2 is a conceptual diagram illustrating the implantable medical device (IMD) and leads of the system shown in FIG. 1 in greater detail.

FIG. 2 is a conceptual diagram illustrating IMD 16 and leads 18, 20, and 22 of system 10 in greater detail. In the illustrated example, bipolar electrodes 40 and 42 are located adjacent to a distal end of lead 18. In addition, bipolar electrodes 44 and 46 are located adjacent to a distal end of lead 20, and bipolar electrodes 48 and 50 are located adjacent to a distal end of lead 22.

In the illustrated example, electrodes 40, 44 and 48 take the form of ring electrodes, and electrodes 42, 46 and 50 may take the form of extendable helix tip electrodes mounted retractably within insulative electrode heads 52, 54 and 56, respectively. Leads 18, 20, 22 also include elongated electrodes 62, 64, 66, respectively, which may take the form of a coil. In some examples, each of the electrodes 40, 42, 44, 46, 48, 50, 62, 64 and 66 is electrically coupled to a respective conductor within the lead body of its associated lead 18, 20, 22, and thereby coupled circuitry within IMD 16.

In some examples, IMD 16 includes one or more housing electrodes, such as housing electrode 4 illustrated in FIG. 2, which may be formed integrally with an outer surface of hermetically-sealed housing 8 of IMD 16 or otherwise coupled to housing 8. In some examples, housing electrode 4 is defined by an uninsulated portion of an outward facing portion of housing 8 of IMD 16. Other division between insulated and uninsulated portions of housing 8 may be employed to define two or more housing electrodes. In some examples, a housing electrode comprises substantially all of housing 8.

As described in further detail with reference to FIG. 3, housing 8 encloses a signal generator that generates therapeutic stimulation, such as cardiac pacing, cardioversion and defibrillation pulses, as well as a sensing module for sensing electrical signals attendant to the depolarization and repolarization of heart 12. Housing 8 may also enclose a heart sound sensor that generates an electrical signal based on sensed heart sounds. The heart sound sensor may be enclosed within housing 8. Alternatively, the heart sound sensor may be integrally formed with an outer surface of housing 8, carried on a lead coupled to IMD 16, such as one or more leads 18, 20 and 22, or be a remote sensor that wireless communicates with IMD 16, programmer 24, or any other device described herein.

IMD 16 senses electrical signals attendant to the depolarization and repolarization of heart 12 via electrodes 4, 40, 42, 44, 46, 48, 50, 62, 64 and 66. IMD 16 may sense such electrical signals via any bipolar combination of electrodes 40, 42, 44, 46, 48, 50, 62, 64 and 66. Furthermore, any of the electrodes 40, 42, 44, 46, 48, 50, 62, 64 and 66 may be used for unipolar sensing in combination with housing electrode 4.

In some examples, IMD 16 delivers pacing pulses via bipolar combinations of electrodes 40, 42, 44, 46, 48 and 50 to produce depolarization of cardiac tissue of heart 12. In some examples, IMD 16 delivers pacing pulses via any of electrodes 40, 42, 44, 46, 48 and 50 in combination with housing electrode 4 in a unipolar configuration. Furthermore, IMD 16 may deliver cardioversion or defibrillation pulses to heart 12 via any combination of elongated electrodes 62, 64, 66, and housing electrode 4.

The illustrated numbers and configurations of leads 18, 20, and 22 and electrodes are merely examples. Other configurations, i.e., number and position of leads and electrodes, are possible. In some examples, system 10 may include an additional lead or lead segment having one or more electrodes positioned at different locations in the cardiovascular system for sensing and/or delivering therapy to patient 14. For example, instead of or in addition to leads intracardiac leads 18, 20 and 22, system 10 may include one or more epicardial or subcutaneous leads not positioned within the heart. As another example, system 10 may include an additional lead that carries a heart sound sensor positioned such that signals generated by the heart sound sensor include heart sounds.

Figure 3:
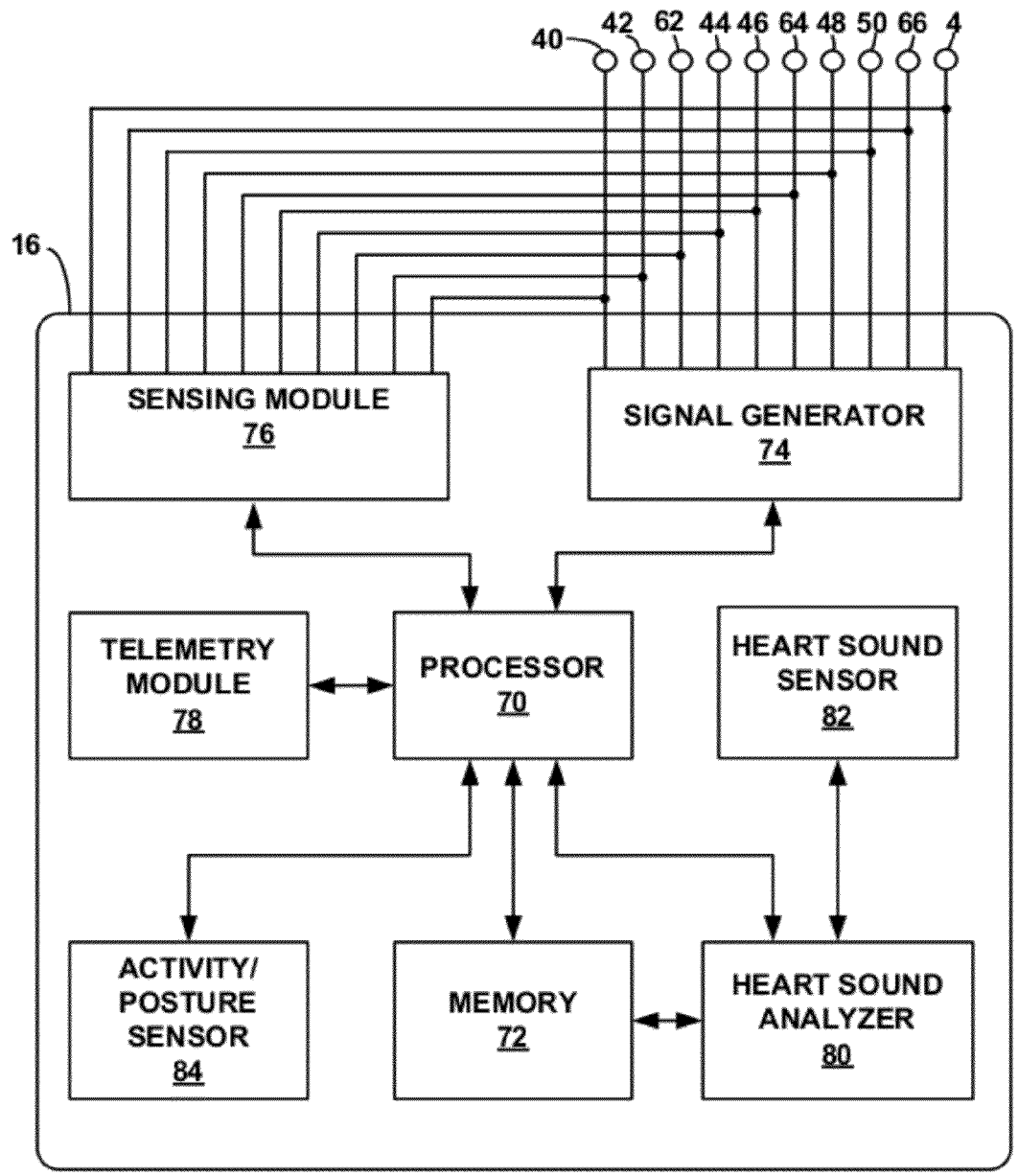
FIG. 3 is a block diagram illustrating an example configuration of the IMD in FIG. 1.

FIG. 3 is a block diagram illustrating an example configuration of IMD 16. In the illustrated example, IMD 16 includes a processor 70, memory 72, signal generator 74, sensing module 76, telemetry module 78, heart sound analyzer 80, heart sound sensor 82 and activity and/or posture sensor 84. Memory 72 includes computer-readable instructions that, when executed by processor 70, causes IMD 16 and processor 70 to perform various functions attributed to IMD 16 and processor 70 herein. Memory 72 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processor 70 may include any one or more of a microprocessor, a controller, a digital signal processor (DSP), an application specific integrated circuit (ASIC), a field-programmable gate array (FPGA), or equivalent discrete or analog logic circuitry. In some examples, processor 70 may include multiple components, such as any combination of one or more microprocessors, one or more controllers, one or more DSPs, one or more ASICs, or one or more FPGAs, as well as other discrete or integrated logic circuitry. The functions attributed to processor 70 herein may be embodied as software, firmware, hardware or any combination thereof. Generally, processor 70 controls signal generator 74 to deliver stimulation therapy to heart 12 of patient 14 according to a selected one or more of therapy programs or parameters, which may be stored in memory 72. As an example, processor 70 may control signal generator 74 to deliver electrical pulses with the amplitudes, pulse widths, frequency, or electrode polarities specified by the selected one or more therapy programs.

Signal generator 74 is configured to generate and deliver electrical stimulation therapy to patient 12. As shown in FIG. 3, signal generator 74 is electrically coupled to electrodes 4, 40, 42, 44, 46, 48, 50, 62, 64, and 66, e.g., via conductors of the respective leads 18, 20, and 22 and, in the case of housing electrode 4, within housing 8. For example, signal generator 74 may deliver pacing, defibrillation or cardioversion pulses to heart 12 via at least two of electrodes 4, 40, 42, 44, 46, 48, 50, 62, 64, and 66. In other examples, signal generator 74 delivers stimulation in the form of signals other than pulses, such as sine waves, square waves, or other substantially continuous time signals.

Signal generator 74 may include a switch module (not shown) and processor 70 may use the switch module to select, e.g., via a data/address bus, which of the available electrodes are used to deliver the electrical stimulation. The switch module may include a switch array, switch matrix, multiplexer, or any other type of switching device suitable to selectively couple stimulation energy to selected electrodes. Electrical sensing module 76 monitors electrical cardiac signals from any combination of electrodes 4, 40, 42, 44, 46, 48, 50, 62, 64, and 66. Sensing module 76 may also include a switch module which processor 70 controls to select which of the available electrodes are used to sense the heart activity, depending upon which electrode combination is used in the current sensing configuration.

Sensing module 76 may include one or more detection channels, each of which may comprise an amplifier. The detection channels may be used to sense the cardiac signals. Some detection channels may detect events, such as R-waves or P-waves, and provide indications of the occurrences of such events to processor 70. One or more other detection channels may provide the signals to an analog-to-digital converter, for conversion into a digital signal for processing or analysis by processor 70.

For example, sensing module 76 may comprise one or more narrow band channels, each of which may include a narrow band filtered sense-amplifier that compares the detected signal to a threshold. If the filtered and amplified signal is greater than the threshold, the narrow band channel indicates that a certain electrical cardiac event, e.g., depolarization, has occurred. Processor 70 then uses that detection in measuring frequencies of the sensed events.

In one example, at least one narrow band channel may include an R-wave or P-wave amplifier. In some examples, the R-wave and P-wave amplifiers may take the form of an automatic gain controlled amplifier that provides an adjustable sensing threshold as a function of the measured R-wave or P-wave amplitude. Examples of R-wave and P-wave amplifiers are described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety.

In some examples, sensing module 76 includes a wide band channel which may comprise an amplifier with a relatively wider pass band than the narrow band channels. Signals from the electrodes that are selected for coupling to this wide-band amplifier may be converted to multi-bit digital signals by an analog-to-digital converter (ADC) provided by, for example, sensing module 76 or processor 70. Processor 70 may analyze the digitized versions of signals from the wide band channel. Processor 70 may employ digital signal analysis techniques to characterize the digitized signals from the wide band channel to, for example, detect and classify the patient's heart rhythm.

Processor 70 may detect and classify the patient's heart rhythm based on the cardiac electrical signals sensed by sensing module 76 employing any of the numerous signal processing methodologies known in the art. For example, processor 70 may maintain escape interval counters that may be reset upon sensing of R-waves by sensing module 76. The value of the count present in the escape interval counters when reset by sensed depolarizations may be used by processor 70 to measure the durations of R-R intervals, which are measurements that may be stored in memory 72. Processor 70 may use the count in the interval counters to detect a tachyarrhythmia, such as ventricular fibrillation or ventricular tachycardia. A portion of memory 72 may be configured as a plurality of recirculating buffers, capable of holding series of measured intervals, which may be analyzed by processor 70 to determine whether the patient's heart 12 is presently exhibiting atrial or ventricular tachyarrhythmia.

In some examples, processor 70 may determine that tachyarrhythmia has occurred by identification of shortened R-R interval lengths. Generally, processor 70 detects tachycardia when the interval length falls below 360 milliseconds (ms) and fibrillation when the interval length falls below 320 ms.

These interval lengths are merely examples, and a user may define the interval lengths as desired, which may then be stored within memory 72. This interval length may need to be detected for a certain number of consecutive cycles, for a certain percentage of cycles within a running window, or a running average for a certain number of cardiac cycles, as examples.

In some examples, an arrhythmia detection method may include any suitable tachyarrhythmia detection algorithms. In one example, processor 70 may utilize all or a subset of the rule-based detection methods described in U.S. Pat. No. 5,545,186 to Olson et al., entitled, "PRIORITIZED RULE BASED METHOD AND APPARATUS FOR DIAGNOSIS AND TREATMENT OF ARRHYTHMIAS," which issued on Aug. 13, 1996, or in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998. U.S. Pat. No. 5,545,186 to Olson et al. U.S. Pat. No. 5,755,736 to Gillberg et al. is incorporated herein by reference in their entireties. However, other arrhythmia detection methodologies may also be employed by processor 70 in other examples. For example, EGM morphology may be considered in addition to or instead of interval length for detecting tachyarrhythmias.

Generally, processor 70 detects a treatable tachyarrhythmia, such as VF, based on the EGM, e.g., the R-R intervals and/or morphology of the EGM, and selects a therapy to deliver to terminate the tachyarrhythmia, such as a defibrillation pulse of a specified magnitude. The detection of the tachyarrhythmia may include a number of phases or steps prior to delivery of the therapy, such as first phase, sometimes referred to as detection, in which a number of consecutive or proximate R-R intervals satisfies a first number of intervals to detect (NID) criterion, a second phase, sometimes referred to as confirmation, in which a number of consecutive or proximate R-R intervals satisfies a second, more restrictive NID criterion. Tachyarrhythmia detection may also include confirmation based on EGM morphology or other sensors subsequent to or during the second phase. Again, in some cases, processor 70 may mistakenly classify the patient's heart rhythm as a treatable tachyarrhythmia, e.g., as a result of a noisy EGM.

To avoid or reduce delivery of therapy in response to a mistakenly classified EGM, IMD 16 also includes heart sound sensor 82 and heart sound analyzer 80. Heart sound sensor 82 generates an electrical signal based on sensed heart sounds of patient 14, and may be implemented as a piezoelectric sensor, a microphone, an accelerometer, or other type of acoustical sensor. In some examples, heart sound sensor 82 may comprise more than one sensor. For example, heart sound sensor 82 may comprise multiple accelerometer devices.

In the illustrated example, heart sound sensor 82 is enclosed within housing 8 of IMD 16. In some examples, heart sound sensor 82 may be formed integrally with an outer surface of housing 8. In other examples, heart sound sensor 82 is located on a lead that is coupled to IMD 16 or may be implemented as a remote sensor that wirelessly communicates with IMD 16. In any case, heart sound sensor 82 is electrically or wirelessly coupled to circuitry contained within housing 8 of IMD 16.

Heart sound analyzer 80 receives the electrical signal generated by heart sound sensor 82. In one example, heart sound analyzer 80 processes the sensor signal to detect heart sounds, classifies the detected heart sounds as either normal or abnormal, and generates an indication that the heart rhythm of the patient is either treatable or non-treatable based on the classification of one or more of the detected heart sounds. In such an example, heart sound analyzer 80 processes the sensor signal to generate an envelope signal, applies an algorithm that uses an adaptively decaying threshold to detect heart sounds within the envelope signal, extracts heart sound features from the detected heart sounds, and classifies the detected heart sounds as normal or abnormal based on the heart sound features. The operation of heart sound analyzer 80 in accordance with this example method is described in greater detail with respect to FIGS. 4-9. In any case, the heart sound based indication may be output to processor 70, which may allow or withhold the therapy selected based on an EGM tachyarrhythmia determination based on the indication.

In some examples, IMD 16 performs these steps prior to delivering any therapy, such as anti-tachycardia pacing (ATP), to the heart of the patient. In other examples, IMD 16 analyzes heart sounds or other aspects of the heart sound signal during delivery of pacing pulses, e.g., ATP. For example, IMD 16 may classify the cardiac rhythm as treatable or non-treatable based on whether the delivery of pacing pulses results in heart sounds that are classified as normal, and selectively deliver or withhold therapy, such as cardioversion or defibrillation, based on the classification. In some examples, IMD 16 delivers the electrical pulses, e.g., ATP, during confirmation phase of tachyarrhythmia detection. In other examples, IMD 16 may deliver ATP to the patient in response to heart sound analyzer 80 indicating that the heart rhythm is treatable based on an analysis of unpaced heart sounds.

Signal generator 74 may deliver the pacing pulses at a known rate. Heart sound analyzer 80 may then process the heart sound signal received from heart sound sensor 82 during the pacing to determine if the pacing results in normal heart sounds. Heart sound analyzer 80 determines whether to deliver cardioversion or defibrillation based on the analysis. The operation of heart sound analyzer 80 in accordance with this additional or alternative example is described in greater detail with respect to FIG. 20

Although processor 70 and heart sound analyzer 80 are illustrated as separate modules in FIG. 3, processor 70 and heart sound analyzer 80 may be incorporated in a single processing unit. Heart sound analyzer 80, and any of its components discussed in greater detail below, may be a component of or module executed by processor 70.

Furthermore, the components of and functionality provided by a heart sound analyzer 80 are described herein with respect to examples in which heart sound analyzer 80 is located within IMD 16. However, it is understood that any one or more heart sound analyzers 80 may be individually or collectively provided by any one or more devices, such as IMD 16 and programmer 24, to individually or collectively provide the functionality described herein. Programmer 24 may receive electrical signals generated by heart sound sensor 4 from IMD 16 in embodiments in which programmer 24 includes a heart sound analyzer.

As illustrated in FIG. 3, IMD 16 may also include an activity and/or posture sensor 84. Activity and/or posture sensor 84 may, for example, take the form of one or more accelerometers, or any other sensor known in the art for detecting activity, e.g., body movement or footfalls, or posture. In some examples, activity and/or posture sensor 84 may comprises a three-axis accelerometer. In some examples, heart sound sensor 82 and activity and/or posture sensor 84 may comprise one or more common accelerometers. As will be described in greater detail below with reference to FIGS. 17-19, processor 70 or heart sound analyzer 80 may use signals from activity and/or posture sensor 84 in various aspects of the heart sound analysis.

Telemetry module 78 includes any suitable hardware, firmware, software or any combination thereof for communicating with another device, such as programmer 24 (FIG. 1). Under the control of processor 70, telemetry module 78 may receive downlink telemetry from and send uplink telemetry to programmer 24 with the aid of an antenna, which may be internal and/or external. In some examples, processor 70 may transmit cardiac signals, e.g., ECG signals, produced by sensing module 76 and/or signals generated by heart sound sensor 82 to programmer 24. Processor 70 may also generate and store marker codes indicative of different cardiac events that sensing module 76 or heart sound analyzer 80 detects, and transmit the marker codes to programmer 24. An example IMD with marker-channel capability is described in U.S. Pat. No. 4,374,382 to Markowitz, entitled, "MARKER CHANNEL TELEMETRY SYSTEM FOR A MEDICAL DEVICE," which issued on Feb. 15, 1983 and is incorporated herein by reference in its entirety. Information which processor 70 may transmit to programmer 24 via telemetry module 78 may also include indications of treatable rhythms, and indications of non-treatable rhythms in which the EGM based indication indicated that the rhythm was treatable and the heart sound based indication indicated that the rhythm was non-treatable. Such information may be included as part of a marker channel with an EGM.

Figure 4:
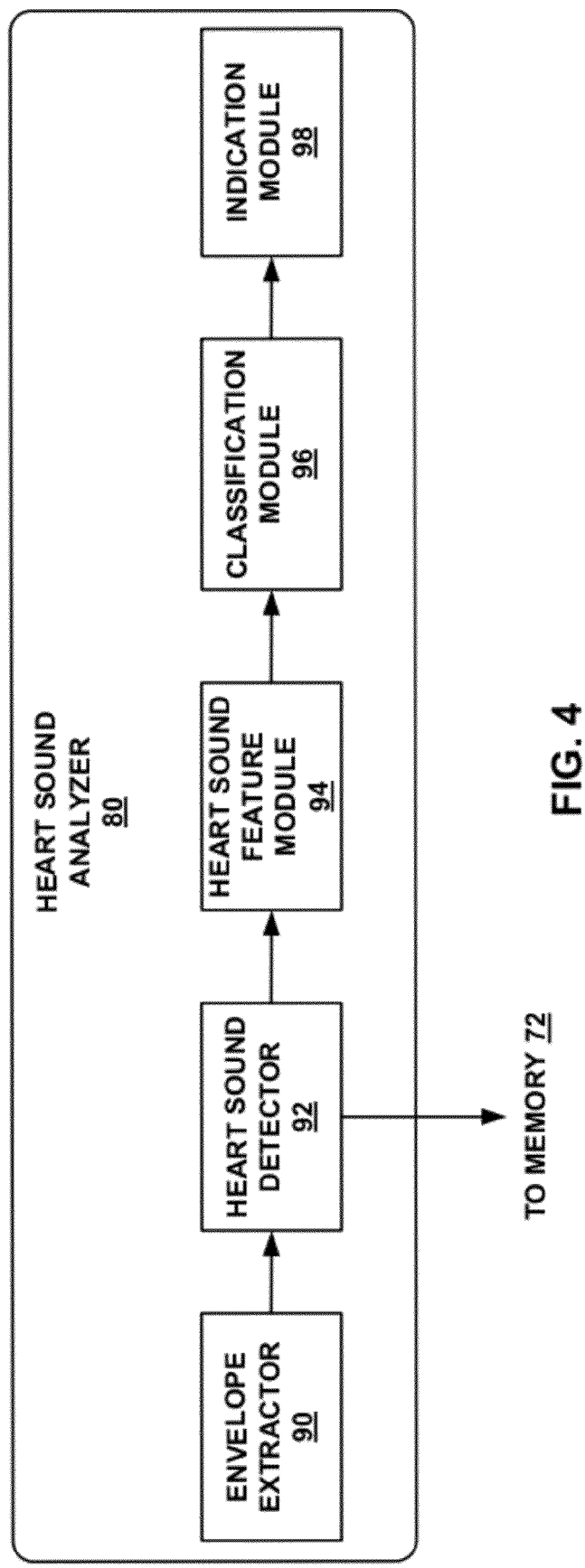
FIG. 4 is a block diagram illustrating an example configuration of a heart sound analyzer shown in FIG. 3.

FIG. 4 is a block diagram illustrating an example configuration of heart sound analyzer 80. As illustrated in FIG. 4, heart sound analyzer 80 may include an envelope extractor 90, heart sound detector 92, heart sound feature module 94, classification module 96, and indication module 98.

Envelope extractor 90 receives an electrical signal from heart sound sensor 82. The electrical signal may be digitized and parsed into segments of predetermined length. As an example, the electrical signal generated by heart sound sensor 82 may be sampled at a 256 Hertz (Hz) rate and parsed into segments including 100 or more sample points. Generally, envelope extractor 90 processes the received signal to extract an envelope, i.e., generate an envelope signal from the received signal.

In some examples, envelope extractor 90 band pass filters, rectifies, and smoothes the sensor signal before extracting the envelope signal. For example, envelope extractor 90 may include a high pass filter, e.g., a 40 Hz high pass filter, and a low pass filter, such as a 70 Hz low pass filter, to remove unwanted signal components from the heart sound sensor signal. In some examples a first order infinite impulse response (IIR) high pass filter with a cutoff frequency of 40 Hz and a third order IIR low pass filter with a cutoff frequency of 70 Hz may be used. In some examples, analog filtering of the heart sound sensor signal may additionally or alternatively be performed prior to digitization of the signal and receipt by envelope extractor 90. As discussed above, IMD 16 may include analog-to-digital conversion circuitry.

Envelope extractor 90 may also, in some examples, include rectification circuitry and circuitry that sums the rectified signal with left-shifted and right-shifted rectified signals in order to smooth the rectified signal. In this manner, envelope extractor may approximately apply an analytic function transform to the signal for envelope extraction. In other examples, envelope extractor 90 may use other methods to generate the envelope signal, such as the normalized Shannon Energy, true Hilbert transform, or rectifying the derivative of the signal followed by moving window integration of the rectified derivative. In such examples, envelope extractor 90 extracts or generates the envelope signal of the processed signal, i.e., the band pass filtered, rectified, and smoothed signal. Extraction of the envelope signal may further include application of a box-car filter, such as a 16 point box-car filter, to the band pass filtered, rectified, and smoothed signal. Envelope extractor 90 outputs the envelope signal to heart sound detector 92. A more detailed description for generating an envelope signal for the sensor signal is provided in FIG. 7.

Heart sound detector 92 utilizes an algorithm to detect heart sounds within the envelope signal. Generally, heart sound detector 92 identifies the local maximums of the envelope signal. In order to identify the local maximums that correspond to heart sounds, heart sound detector 92 may utilize an adaptively decaying threshold. The adaptively decaying threshold is determined based on the running average of detected heart sound amplitudes, the running average of the envelope signal amplitude, and the mean heart sound-to-heart sound interval. Heart sound detector 92 compares the envelope signal to the adaptively decaying threshold to identify the local maximums. Heart sound detector 92 may store markers, referred to as "heart sound markers," for the identified local maximums within memory 72 or provide the heart sound markers directly to heart sound feature module 94. An example algorithm for detecting heart sounds within an envelope signal is described in greater detail with respect to FIG. 8.

Heart sound feature module 94 extracts features of the detected heart sounds. Example heart sound features include the mean period ratio (MPR) and matching score (MS) for a detected heart sound. The MPR for a detected heart sound is the period of the detected heart sound divided by the mean period of one or more template heart sounds. The MS may be determined using template matching schemes that compare detected heart sounds to template heart sounds, such as a wavelet template matching scheme or a "bounded template" matching scheme. An example wavelet template matching scheme is disclosed in U.S. Pat. No. 6,393,316 issued to Jeff Gillberg. An example bounded template matching scheme is disclosed in a commonly assigned and copending patent application Ser. No. 12/357,868, filed Jan. 22, 2009, entitled "A Blurred Template Approach for Arrhythmia Detection," by Xin Zhang, Mark Brown, Xusheng Zhang, and Jeff Gillberg.

In some examples, template heart sounds used for determining the MPR and MS may be example heart sounds that are loaded into heart sound feature module 94. In other examples, template heart sounds may be heart sounds that were measured during a baseline interval of the patient. That is, the template heart sounds may be obtained from patient 14 during an identified or predetermined time period during which the patient is known to have a normal cardiac rhythm. In some examples, a time period for detecting template heart sounds may be determined using techniques described below with reference to FIG. 17.

Heart sound feature module 94 may use a heart sound marker from heart sound detector 92 to center a window, e.g., a 48 point or sample window, at a detected heart sound and use the resulting segment of samples to determine the MPR and MS. For example, heart sound feature module 94 may determine the period of the band-pass filtered signal segment and use it to determine the MPR, and may compare the extracted envelope signal segment to a stored template to determine the MS. Heart sound feature module 94 may then provide the MPR and MS to classification module 96.

Figure 9:
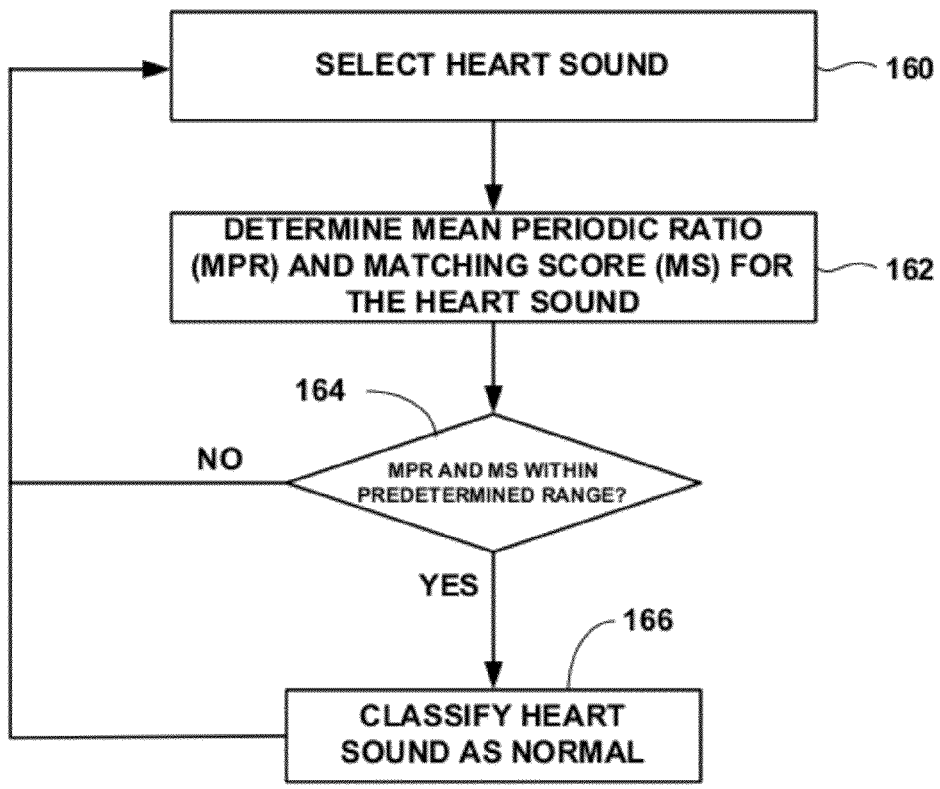
FIG. 9 is a flow diagram illustrating an example method for extracting features of detected heart sounds, and classifying the detected heart sounds based on the heart sound features.

Classification module 96 classifies each of the detected heart sounds as either normal or abnormal based on the corresponding heart sound feature values. Classification of the heart sounds as normal or abnormal may be based on whether the features, e.g., the MPR and MS values, are within a predetermined range, or above or below a predetermined threshold. FIG. 9 illustrates an example method that may be performed by heart sound feature module 94 and classification module 96 to determine heart sound features and classify heart sounds based on the heart sound features. An example graph showing a predetermined range of MPR and MS values is provided in FIG. 16.

Indication module 98 receives the classification information for each of the detected heart sounds from classification module 96, and generates an indication whether the cardiac rhythm is treatable or non-treatable, e.g., whether to deliver or withhold the therapy scheduled for delivery to terminate the EGM indicated tachyarrhythmia, based on the received information. Generally, indication module 98 may generate the indication based on one or more heart sounds. As an example, indication module 98 may generate an indication that a rhythm is treatable when a threshold number of consecutive or proximate heart sounds, e.g., less than six of the last eight heart sounds, are classified as normal, and generate an indication that a rhythm is non-treatable when at least the threshold number of heart sounds are classified as normal. In other examples, the threshold number may be a threshold number of abnormal heart sounds. In still other examples, classification module 96 may classify heart beats as normal or abnormal based on the classification of one or more heart sounds within each of the beats, and indication module may provide the indication as described based on a threshold number of normal or abnormal heart beats. Indication module 98 provides an indication to processor 70, which selectively delivers therapy based on the heart sound based indication received from indication module 98.

Figure 5:
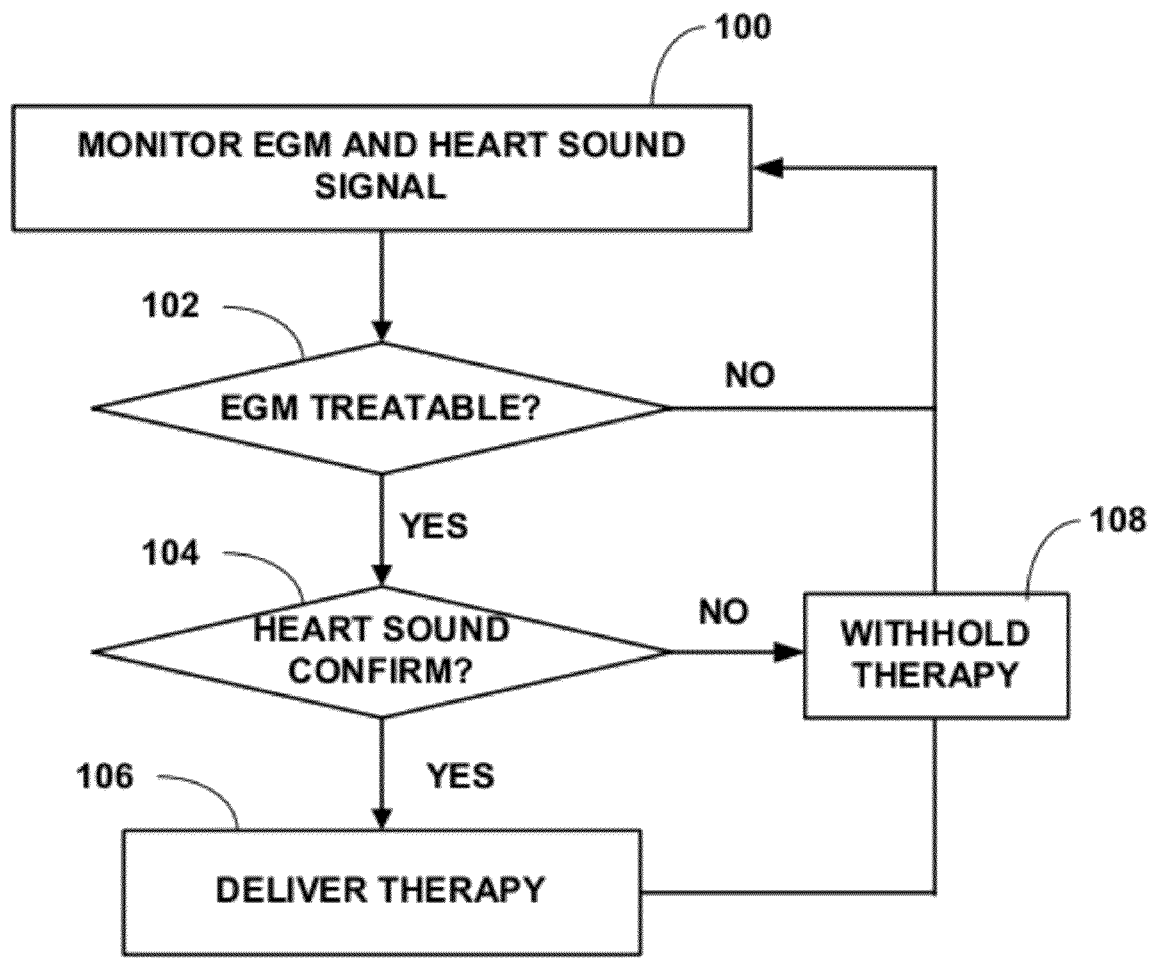
FIG. 5 is a flow diagram illustrating an example method for allowing or withholding a tachyarrhythmia therapy based on heart sound sensing.

FIG. 5 is a flow diagram illustrating an example method for allowing or withholding a tachyarrhythmia therapy based on heart sound sensing. The example method is described with respect to IMD 16 and its components shown in FIG. 3, but in other examples may be practiced, at least in part, by another device, such as programmer 24.

According to the illustrated example, processor 70 monitors the EGM and heart sound analyzer 80 monitors a signal from one or more heart sound sensors (100). If processor 70 detects a treatable cardiac rhythm, e.g., VF, based on the EGM (102), processor looks to heart sound analyzer 80 for an indication confirming that the rhythm is treatable (104). If heart sound analyzer 80 provides an indication that the rhythm is treatable, processor 70 controls signal generator 74 to deliver the therapy, e.g., defibrillation pulse (106). If heart sound analyzer 80 provides an indication that the rhythm is not treatable, processor 70 withholds the therapy, e.g., does not control signal generator 74 to deliver the scheduled therapy (108). Processor 70 and analyzer 80 may then continue to monitor the EGM and heart sound signals, respectively (100).

Heart sound sensor 82 may generate a heart sound signal, and heart sound analyzer 80 may analyze the heart sound signal substantially continuously, or only upon a detection of a treatable tachyarrhythmia based on the EGM by processor 70. In some examples, heart sound sensor 82 may generate the heart sound signal or heart sound analyzer 80 may analyze the signal in response to processor 70 determining that a first detection phase criteria is met by the EGM. In such examples, heart sound sensor 82 may generate the heart sound signal or heart sound analyzer 80 may analyze the signal during a second confirmation phase analysis of the EGM by processor 70.

Figure 6:
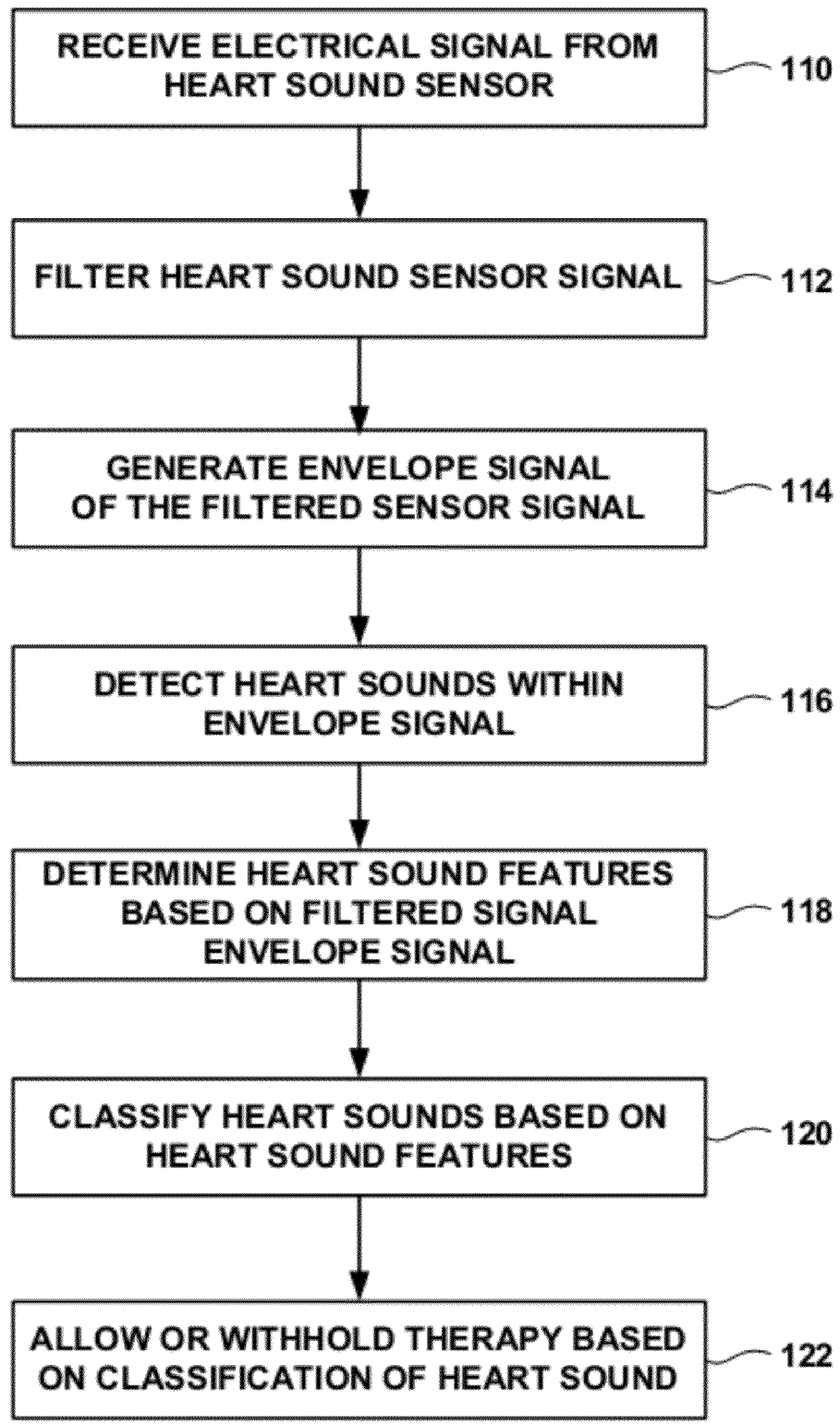
FIG. 6 is a flow diagram illustrating an example method for allowing or withholding a tachyarrhythmia therapy based on detection and classification of heart sounds.

FIG. 6 is a flow diagram illustrating an example method for allowing or withholding a tachyarrhythmia therapy based on detection and classification of heart sounds. The example method is described with respect to heart sound analyzer 80 and its components, and processor 70, but it should be understood that the example method may be performed by any one or more devices, processors, or components described herein.

According to the example method, heart sound analyzer 80 receives an electrical signal from heart sound sensor 82 (110). Heart sound analyzer 80 or another component of IMD 16 filters, e.g., band pass filters, the heart sound signal (112). Envelope extractor 90 receives the filtered sensor signal and processes the sensor signal to generate the envelope signal of the filtered sensor signal (114). A more detailed description for processing the received electrical signal to generate the envelope signal is provided with respect to FIG. 7.

Heart sound detector 92 detects heart sounds within the envelope signal (116). In some examples, heart sound detector 92 detects the heart sounds using an algorithm that uses an adaptively decaying threshold. Detecting heart sounds within the envelope signal may include marking the heart sounds in time. An example algorithm for detecting heart sounds within the envelope signal is described in greater detail with respect to FIG. 8.

Heart sound feature module 94 determines heart sound features for the detected heart sounds based on the envelope signal and the filtered heart sound signal (118). For example, heart sound feature module 94 may determine an MPR and MS for the detected heart sounds. Classification module 96 classifies each of the detected heart sounds as either normal or abnormal based on the heart sound features, e.g., the MPR and MS (120). As an example, classification module 96 may compare the MPR and MS of a detected heart sound to a predetermined range of values. When the MPR and MS of the detected heart sound is within the predetermined range of values, classification module 96 may classify the detected heart sound as normal. However, if the MPR and MS of the detected heart sound are not within the predetermined range of values, the detected heart sound may be classified as abnormal.

Indication module 98 provides an indication to processor 70 of whether the heart rhythm is treatable or non-treatable based on the classification of one or more of the heart sounds. For example, indication module 98 may indicate that the heart rhythm is non-treatable when at least six of the last eight heart sounds are classified as normal. Processor 70 allows or withholds a therapy selected based on the EGM-based detection based on the classification of the heart sounds, e.g., based on the indication from indication module 98 (122).

Figure 7:
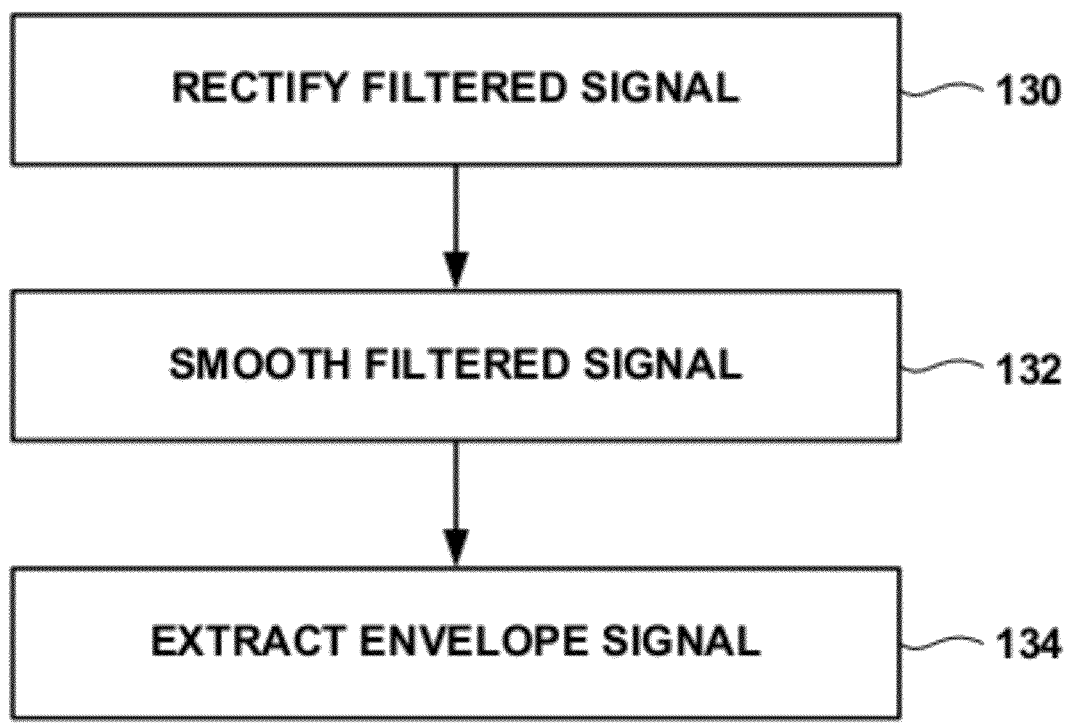
FIG. 7 is a flow diagram illustrating an example method for generating an envelope signal based on a heart sound signal.

FIG. 7 is a flow diagram illustrating an example method for extracting an envelope signal from the signal output by heart sound sensor 82. Envelope extractor 90 receives the sensor signal, which may be band pass filtered. In some examples, the sensor signal may be converted to a digital signal by an ADC. For example, the sensor signal may be sampled at approximately 256 Hz although other sampling rates are possible. A graph illustrating an example sensor signal is provided in FIG. 11.

The pass band may be approximately 40-70 Hz. In some examples, a first order infinite impulse response (IIR) high pass filter with a cutoff frequency of 40 Hz and a third order IIR low pass filter with a cutoff frequency of 70 Hz may be used. A graph illustrating an example filtered signal is provided in FIG. 12.

Envelope extractor 90 rectifies the filtered signal (130), smoothes the filtered signal (132), and extracts the envelope signal from the rectified and smoothed signal (134). In one example, envelope extractor 90 may smooth the filtered signal by summing together and averaging a left-shifted version of the signal, the initial signal, and a right-shifted version of the signal. Envelope extractor 90 may apply a boxcar filter to the resulting signal to extract the envelope signal. Generally, the number of points used in the boxcar filter may be dependent on the sampling rate. As one example, the boxcar filter may be a 16 point boxcar filter when the sample rate is approximately 256 Hz. A graph illustrating an example envelope signal is provided in FIG. 13.

Other filters or signal processing techniques may be used to extract the envelope signal. In some examples, wavelet transforms may be used instead of or in addition to the bandpass filtering. Wavelet transforms may be considered to be equivalent to a series of bandpass filters with different central frequencies by the same Q (quality) factor under different scales. Wavelet transforms may also allow automatic identification of the wavelet levels which contain heart sound information.

Figure 8:
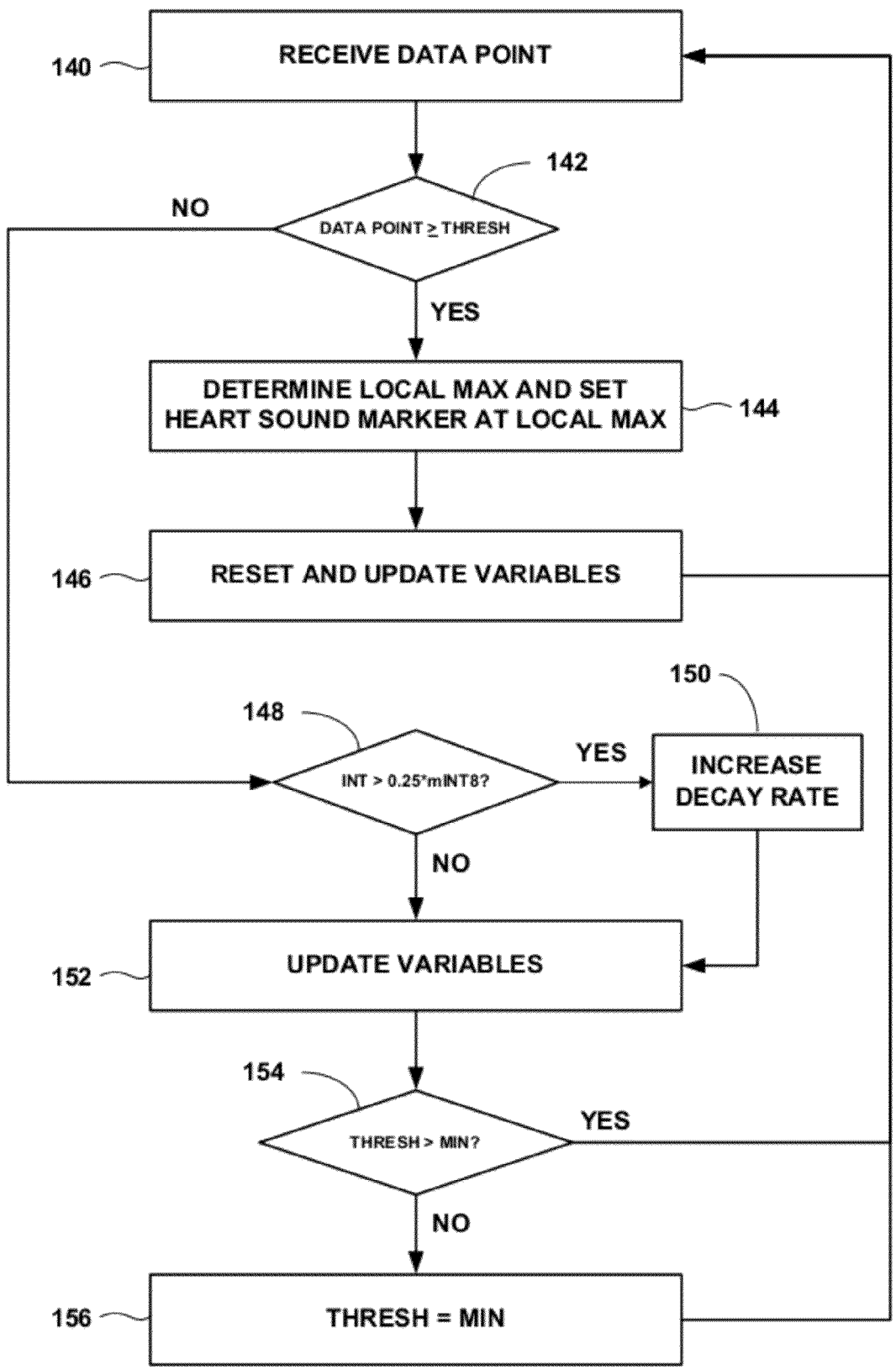
FIG. 8 is a flow diagram illustrating an example method of detecting heart sounds within an envelope signal.

FIG. 8 is a flow diagram illustrating an example method for detecting heart sounds within the envelope signal. Generally, the example method utilizes an adaptively decaying threshold for detecting heat sounds within the envelope signal. The detection threshold adapts for each heart sound interval. That is, the initial value of the detection threshold and the decay rate is calculated for each heart sound interval. In particular, the decay rate is determined based on the running average of the amplitude of the signal peaks for detected heart sounds, the running average of the amplitude of the envelope signal, and the mean heart sound-to-heart sound interval. Accordingly, the detection threshold begins at an initial maximum value for a heart sound interval and decays from that value. In some examples, the detection threshold is controlled such that it does not decay below a minimum value. This prevents incorrectly detecting low amplitude signal peaks as heart sounds. The minimum value is also calculated for each heart sound interval.

Additionally, the decay rate of the adaptively decaying threshold may adapt within a heart sound interval. Specifically, the decay rate may be increased when a heart sound has not been detected within an expected interval. A graph illustrating an example envelope signal with a trace of an example adaptively decaying detection threshold is provided in FIG. 14.

Because of the nature of the adaptively decaying threshold, the example method shown in FIG. 8 uses several variables for tracking parameters of the envelope signal. Examples parameters include SPr, SPc, ASr, ASc, mBB8, MIN, THRESH, and Decay Rate. SPr represents a running average of signal peak amplitudes for detected heart sounds. SPc represents the signal peak amplitude for the currently detected heart sound. ASr represents a running average of the amplitude of the envelope signal for heart sound intervals. ASc represents an average of the amplitude of the envelope signal for the current heart sound interval. mINT8 represents the mean time for the last eight heart sound intervals. MIN represents a minimum value below which the threshold cannot delay. THRESH is the adaptively decaying threshold. Decay Rate is the decay rate for the threshold. INT is the time of the current interval from the most recently detected heart sound. In one example, SPr, ASr, THRESH, and Decay Rate are defined according to the following equations.

$$SPr = 0.5 * SPc + 0.5 * SPr \quad (1)$$

$$ASr = 0.5 * ASc + 0.5 * ASr \quad (2)$$

$$MIN = ASr * 1.5 \quad (3)$$

$$\text{Decay Rate} = \begin{cases} \dfrac{SPr - ASr * 1.125}{mINT8}, & \text{when INT} \leq 1.25 * mINT8, \\ & \text{and no beat was detected} \\ \dfrac{SPr - ASr * 1.125}{mINT8}, & \text{otherwise, where } Asr = 0.5 * Asr \\ & \text{for every } 0.25 * mINT8 \\ & \text{that a beat is not detected} \end{cases} \quad (4)$$

$$THRESH = \quad (5)$$
$$\begin{cases} SPr, & \text{when INT} = 0 \\ THRESH - \text{Decay Rate}, & \text{when INT} > 0 \text{ and } THRESH \geq MIN \\ MIN, & \text{otherwise} \end{cases}$$

With respect to the example method shown in FIG. 8, heart sound detector 92 receives a data point (140) and compares the data point to the detection threshold (THRESH) (142). Heart sound detector 92 may retrieve the data point from memory 72 which stores a digitized envelope signal. When the data point is the first data point for a heart sound interval, i.e., the first data point retrieved from memory after a heart sound has been detected, the detection threshold (THRESH) is equal to SPr, i.e., the amplitude of the just detected heart sound, according to equation 5 provided above.

When the data point is less than the detection threshold, heart sound detector 92 determines whether the interval since the detection of last heart sound is sufficiently long to adapt, e.g., increase, the decay rate. The threshold for adapting the decay rate may be determined based on an average of previous heart sound intervals. In the example method, heart sound detector 92 compares the time of the current interval from the most recently detected heart sound (INT) to the threshold, i.e., 0.25*mINT8 (mINT8 being the mean of the last eight heart sound intervals) in the illustrated example (148). If the current interval time is less than the threshold, i.e., INT is less than 0.25*mINT8, then heart sound detector 92 updates the appropriate variables 152. Updating the variables may include updating the detection threshold, i.e., reducing the detection threshold according to an unadjusted decay rate, updating the averaged signal for the current heart sound interval (ASc), and updating the current interval from the last detected heart sound (INT).

If, however, the current interval is greater than the threshold ("YES" branch of decision block 148), heart sound detector 92 increases the decay rate (150) according to equation 4 provided above and otherwise updates variables (152), such as the running signal average for the interval (ASc) and the current time (INT). By increasing the decay rate, heart sound detector 92 provides a decaying threshold that is adaptive over time, i.e., an adaptively decaying threshold.

Heart sound detector 92 further determines whether the detection threshold (THRESH) is less than the minimum value (MIN) (154). When the detection threshold is less than or equal to the minimum value, heart sound detector 92 sets the detection threshold equal to the minimum value, i.e., THRESH==MIN. Setting the detection threshold equal to the minimum value may prevent incorrectly detecting a low amplitude signal peak as a heart sound. If, however, the detection threshold is greater than the minimum value, the detection threshold has been updated to reflect the correct value for the subsequent data point. Accordingly, heart sound detector 92 may receive a subsequent data point and repeat the steps of the example method as necessary.

When a data point is greater than the detection threshold ("YES" branch of decision block 142), heart sound detector 92 determines the local maximum and sets a heart sound marker at the local maximum (144). Heart sound detector 92 may locate the local maximum using various methods known in the art of signal processing. As one example, heart sound detector 92 may recursively compare subsequent data points to each other. In such an example, the heart sound is detected when a subsequent data point is less than the previous data point. The previous data point is the local maximum and, thus, heart sound detector 92 may set a heart sound marker at that data point. That is, heart sound detector 92 may store a heart sound marker in memory 72 that is used to retrieve that data point. The heart sound marker may, for example, mark the data point in time so that the data point can be retrieved from memory 72 at a later time. In this way, heart sound detector 92 detects heart sounds by marking the data point that is the local maximum for a heart sound interval.

Heart sound detector 92 then resets and updates variables 146 as necessary. For example, heart sound detector 92 may reset the current interval variable (INT) and the variables for current heart sound intervals, such as SPc and ASc, to zero, and update variables that are parameters for multiple intervals, such as SPr, ASr, and mINT8. Heart sound detector 92 may also reset the detection threshold and decay rate accordingly.

In some examples, heart sound detector 92 may retrieve the next data point as the data point approximately 200 milliseconds (ms) following the data point that is the local maximum, i.e., the detected heart sound. This because a heart sound is not expected to be detected during the refractory period following a heart sound. By remaining inoperative during the refractory period, i.e., 200 ms, the possibility of mistakenly detecting a heart sound during this time is eliminated.

Furthermore, in some examples, heart sound detector 92 may monitor the noise floor between detected heart sounds, and adjust the detection threshold based on the noise floor. In this manner, heart sound detector 92 may account for changes in the noise floor which may cause the amplitude of peaks associated with heart sounds to vary on a heart sound-to-heart sound basis. For example, heart sound detector 92 may increase or decrease the initial value of THRESH based on the noise floor during the last heart sound interval, or a mean or median of the noise floor for a number of preceding heart sound intervals. In some examples, heart sound detector 92 increases or decreases the initial value of THRESH based on a comparison of the noise floor during the last heart sound interval to a mean or median of the noise floor for a number of preceding heart sound intervals. The noise floor may be determined using any known technique for determining a noise floor of a signal. In one example, heart sound detector 92 may determine the noise floor for a heart sound interval based on the standard deviation between the end of one detected peak and the beginning of the next detected peak.

FIG. 9 is a flow diagram illustrating an example method for extracting heart sound features, and classifying detected heart sound based on the heart sound features. The steps in the example method shown in FIG. 9 are described as being performed by heart sound feature module 94, and classification module 96, but could be performed by any device, processor, or component described herein.

According to the illustrated example, heart sound feature module 94 selects a heart sound (160) and determines the mean period ratio (MPR) and matching score (MS) for the heart sound (162). Heart sound feature module 94 may select the heart sound by selecting segments of the envelope signal and the filtered signal that is centered on the heart sound. Heart sound feature module 94 may use a window function, centered at the heart sound marker for the selected heart sound, to select the signal segments. The window signal segment may be selected as a 48 point or sample segment, although other sizes are possible.

Heart sound feature module 94 may determine the heart sound features, e.g., the MPR and MS, for the signal segments using various techniques. Heart sound module 94 may, for example, determine the MPR for the segment of the filtered signal by computing the period for the signal segment and dividing the computed value by a mean period value stored in memory. The mean period value may be the mean period of template heart sounds. Heart sound feature module 94 may use a template matching scheme to determine the MS for the envelope signal segment. For example, heart sound feature module 94 may compare the signal segment to template heart sounds using a wavelet template matching scheme or bounded template matching scheme. In any case, heart sound feature module 94 determines values for the MPR and MS of the signal segments.

In the illustrated example, classification module 96 classifies the selected heart sound based on the heart sound features by comparing the MPR and MS values to a predetermined range of values (164). If the MPR and MS are within the predetermined range of values, classification module 96 classifies the heart sound as normal (166). On the other hand, when the MS and MPR values are not within the predetermined range, classification module 96 classifies the heart sound as abnormal. In the example method shown in FIG. 9, classification module 96 takes no action to classify heart sounds as abnormal when the heart sound features are outside the predetermined range. In some examples, classification module 96 may additionally or alternatively classify heart sound as abnormal, for example, by setting a Boolean variable to an appropriate value or by updating a flag variable.

Figure 10:
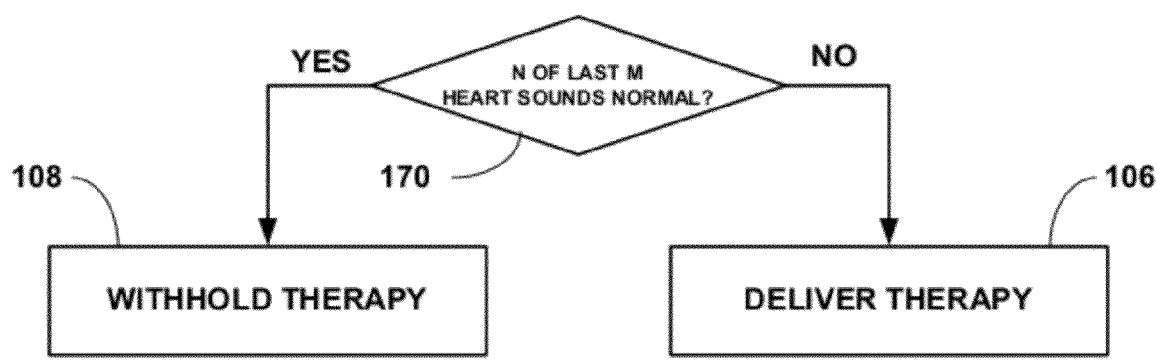
FIG. 10 is a flow diagram illustrating an example method for allowing or withholding a tachyarrhythmia therapy based on the classification of the heart sounds.

FIG. 10 is a flow diagram illustrating an example method for allowing or withholding a tachyarrhythmia therapy based on the classification of the heart sounds. The example method of FIG. 10 is described with respect to indication module 98 and processor 70, but may be performed by any device, processor, or module described herein.

In the example method of FIG. 10, indication module 98 determines whether N of the last M heart sounds, e.g., six of the last eight heart sounds, were classified as normal. Indication module 98 may provide an indication to processor 70 that the heart rhythm of the patient is treatable or non-treatable based on whether this criterion is satisfied. For example, indication module 98 may indicate that the rhythm is non-treatable if the criterion is satisfied, e.g., if the rhythm is predominately normal indicating that the patient is not in fact suffering a treatable tachyarrhythmia. In other examples, indication module 98 may apply other criteria to determine whether the cardiac rhythm is treatable based on the classification of one or more consecutive or proximate heart sounds. If the criterion is satisfied (or not satisfied in other examples) processor 70 withholds the therapy scheduled based on the EGM detection (108). If the criterion is not satisfied (or satisfied in other examples) processor 70 controls signal generator 74 to deliver the therapy (106).

Figure 11:
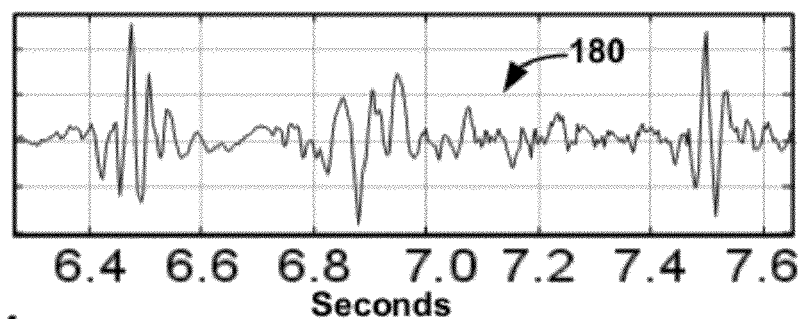
FIG. 11 illustrates an example heart sound signal.

FIG. 11 illustrates an example signal 180 generated by heart sound sensor 4 and may, therefore, be viewed as a raw signal. In particular, signal 180 represents a signal that may be received by heart sound analyzer 80.

Figure 12:
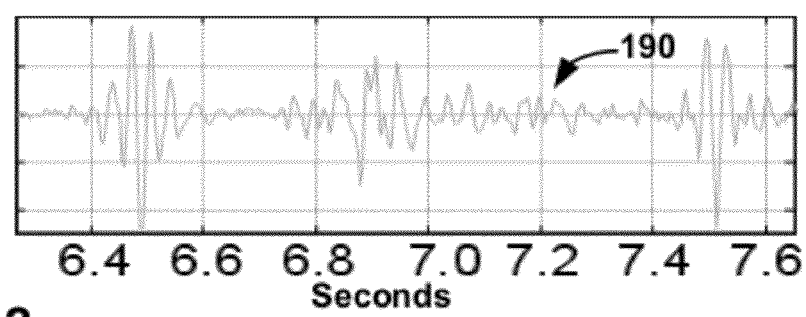
FIG. 12 illustrates an example band pass filtered heart sound signal.

FIG. 12 illustrates an example band pass filtered signal 190. That is, signal 190 represents a band pass filtered version of signal 180. Signal 190 may be further processed, i.e., rectified and smoothed, to generate an envelope signal, such as the envelope signal shown in FIG. 13.

Figure 13:
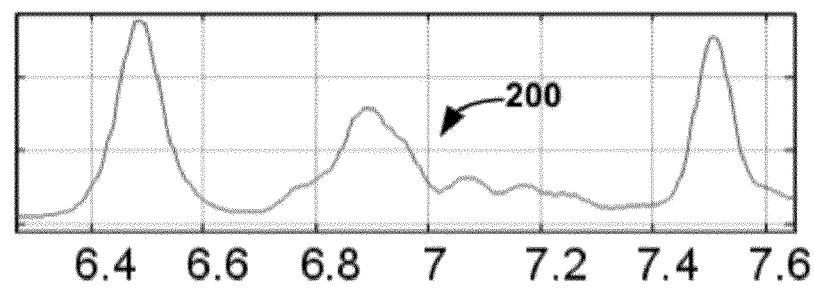
FIG. 13 illustrates an example envelope signal of the filtered heart sound signal.

FIG. 13 illustrates an example envelope signal 200. Accordingly, envelope signal 200 represents a signal that is output by envelope extractor 90.

Figure 14:
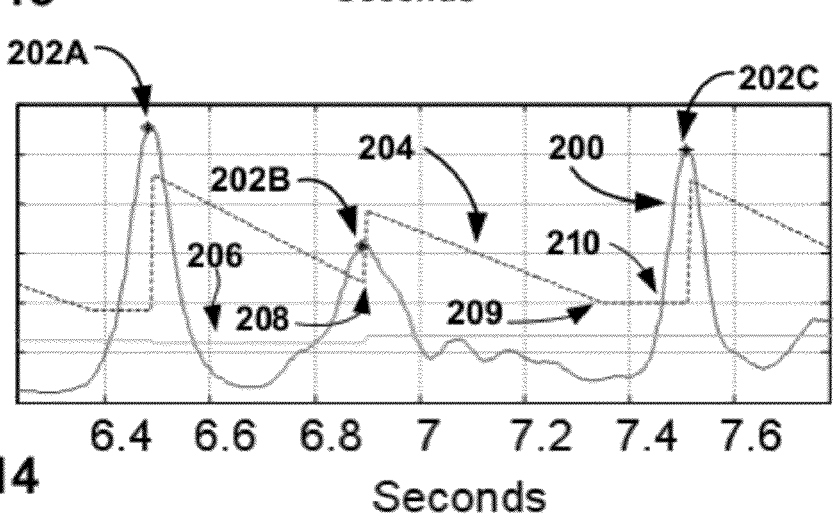
FIG. 14 illustrates an example technique for detecting heart sounds in the envelope signal of FIG. 13.

FIG. 14 illustrates example envelope signal 200 with heart sound markers 202A-C and a trace for the adaptively decaying detection threshold 204. As shown, detected heart sounds are marked with heart sound markers 202A-C at the peak of the detected heart sound. Trace 204 for the detection threshold tracks the value of the detection threshold over time. At each of heart sound markers 202A-C, trace 204 begins at a maximum value and decays, according to the decay rate, until envelope signal 200 exceeds the detection threshold and another heart sound is detected.

As an example, trace 204 has a value equal to SPr, i.e., the running average of signal peaks for detected heart sounds, at heart sound marker 202A. Trace 204 decays from this initial value according to the decay rate that until envelope signal 200 exceeds the detection threshold. In FIG. 14, envelope signal 200 exceeds the detection threshold at point 208. At point 208, the detection algorithm searches for the local maximum and marks the local maximum, or signal peak, with heart sound marker 202B. The value of the detection threshold is again reset according to SPr as reflected in trace 204 resetting to a higher value at heart sound marker 202B.

Again, trace 204 decays according to the new decay rate from heart sound marker 202B until point 209. At point 209 the detection threshold reaches the lower bound (MIN). The detection threshold remains equal to the lower bound until the envelope signal exceeds the lower bound at point 210. Consequently, trace 204 is a horizontal line segment from point 209 until heart sound marker 202C.

FIG. 14 also illustrates noise floor 206. As described above, the detection threshold may be modified based on noise floor 206. For example, the initial value of detection threshold trace 204 after a detected heart sound may be modified based on the noise floor 206.

Figure 15:
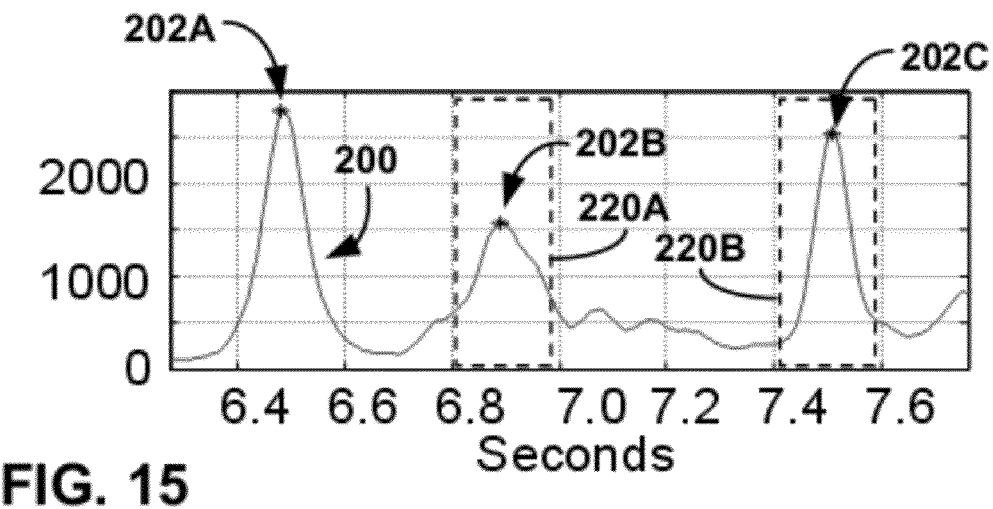
FIG. 15 illustrates the example envelope signal of FIG. 13 with heart sound markers that mark detected heart sounds.

FIG. 15 illustrates an example heart sound feature extraction technique. In particular, FIG. 15 is a graph illustrating windows 220A and 220B used for extracting heart sound features in conjunction with envelope signal 200. Windows 220A and 220B are centered at heart sound markers 202B and 202C, respectively, and define segments of envelope signal 200 that may be used for determining a MS for those segments. The windowed segments of envelope signal 200 may be, for example, 48 point segments centered at heart sound markers. As described above, windows may be similarly centered at heart sound markers to define segments of the band pass filtered signal to determine the MPR for those segments of the filtered signal.

Figure 16:
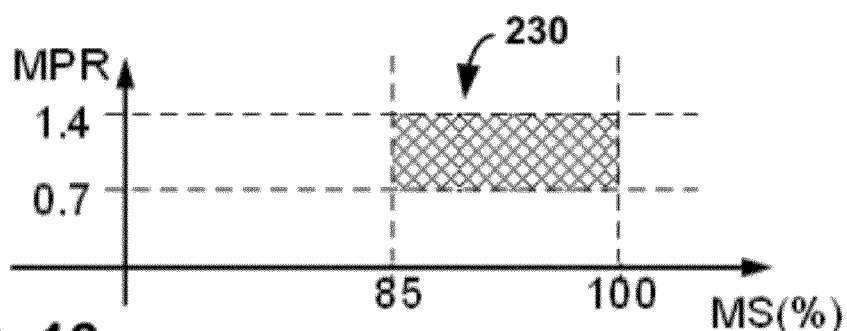
FIG. 16 illustrates an example technique for classifying detected heart sounds based on heart sound features of the detected heart sounds.

FIG. 16 is a graph illustrating an example technique for classifying detected heart sounds based on features of the detected heart sounds. The graph in FIG. 16 plots the MPR along the vertical axis and the MS along the horizontal axis. If the MPR and MS for a detected heart sound fall within region 230, the detected heart sound is classified as a normal heart sound. As previously described, a cardiac rhythm may be determined to be non-treatable when a predetermined number of heart sounds are classified as normal. As an example, a cardiac rhythm may be determined to be non-treatable when six of the last eight heart sounds are classified as normal using the graph in FIG. 16.

Figure 17:
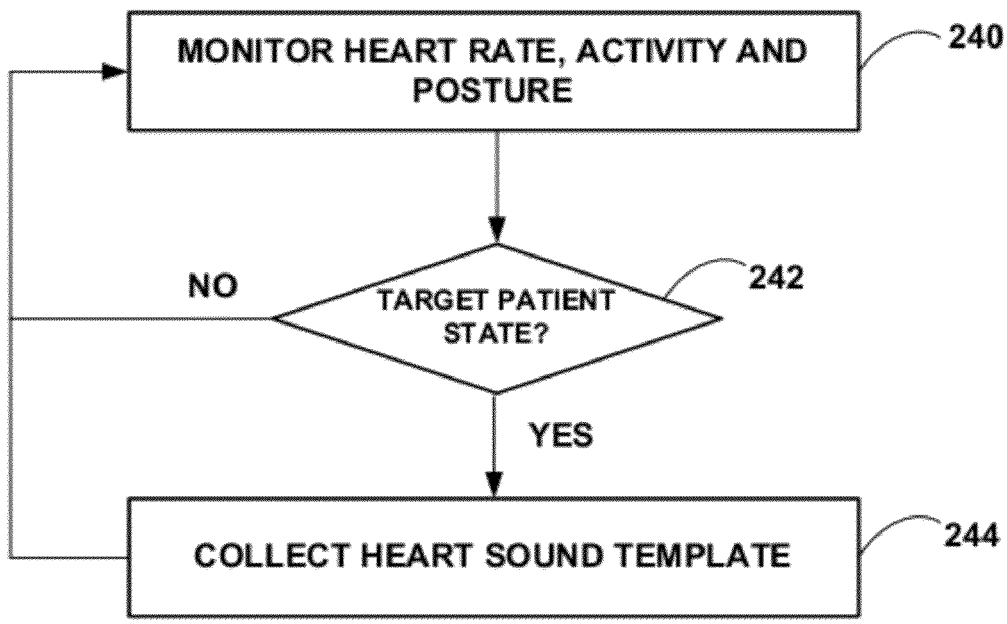
FIG. 17 is a flow diagram illustrating an example method for learning a heart sound template.

FIG. 17 is a flow diagram illustrating an example method for learning a heart sound template. The example method of FIG. 17 is described with respect to heart sound analyzer 80 and processor 70, but may be performed by any device, processor, or module described herein.

As described above, heart sound feature module 94 may compare a segment of an envelope signal for a detected heart sound heart sound to a template heart sound to determine a MS for the detected heart sound. Classification module 96 may classify the detected heart sound as normal or abnormal based, at least in part, on the MS. In some examples, the template heart sound is a baseline heart sound of the patient, rather than a general template heart sound not specific to any patient and useable for many patients, that is known to be normal or abnormal. The template heart sound may be collected during a period in which the patient is detected to be in a state in which the heart sound will likely be normal or abnormal. For example, a normal template heart sound may be collected when the patient is not experiencing tachyarrhythmia, and also not in a state likely to result in noise in the heart sound signal.

According to the example method of FIG. 17, processor 70 monitors one or more patient physiological parameters, such as one or more of heart rate, patient activity, and patient posture (240). Processor 70 may monitor heart rate based on indications received from sensing module 76, which senses cardiac electrical signals, and activity and posture based on signals received from activity posture sensor 84, which may comprise one or more accelerometers, as an example.

Processor 70 determines whether patient 14 is in a target state for collecting a template heart sound, e.g., a normal or abnormal template heart sound, based on the one or more physiological parameters (242). For example, to collect a normal heart sound template, processor 70 may determine whether patient 14 is within a target posture, or in a stable posture, e.g., the patient's posture is not changing at more than a threshold rate or amount. To collect a normal heart sound template, processor 70 may also determine that the activity of patient 14 is low, and/or the heart rate of patient 14 is low, stable, or not tachyarrhythmic. To later detect tachyarrhythmia based on heart sounds, it may be desirable to collect a normal heart sound template when the heart is known to be in a stable and/or not tachyarrhythmic condition. Furthermore, certain postures, or high activity or rapid posture transitions may introduce noise into the heart sound signal, which would be undesirable for determining a template heart sound.

When processor 70 determines that patient 14 is within the target state ("Yes" branch of 242), processor 70 collects the heart sound template, e.g., by directing heart sound analyzer 80 to process a heart sound signal from heart sound sensor 82 (244). For example, processor 70 may direct envelope extractor 90 to extract an envelope signal from the heart sound signal, and direct heart sound detector 92 to detect a heart sound in the envelope signal, and delineate a segment of the envelope signal surrounding the identified heart sound. Processor 70 may store the segment of the envelope signal in memory 72 as a heart sound template for later use by heart sound feature module 94, e.g., for comparison with later detected envelope signal segments using template matching techniques to determine a MS.

Figure 18:
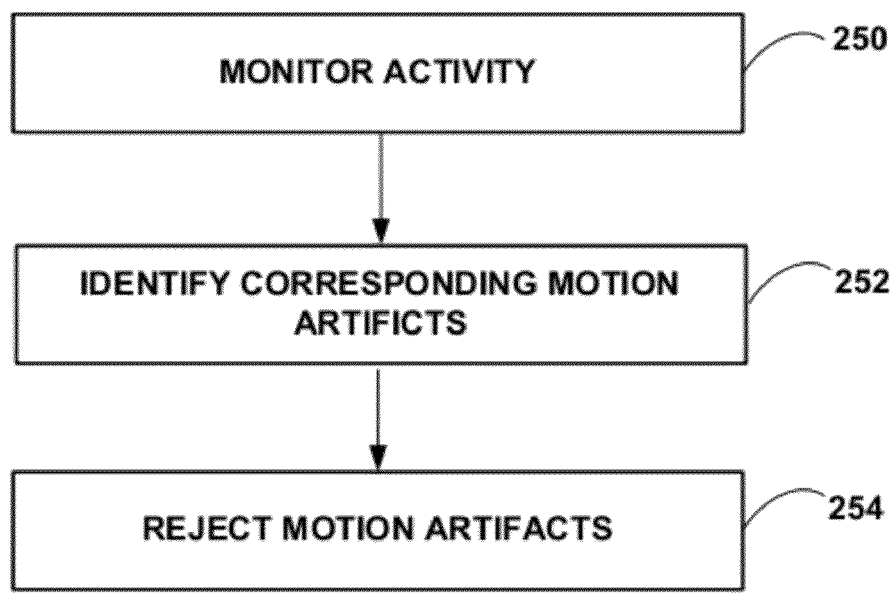
FIG. 18 is a flow diagram illustrating an example method for rejecting motion artifacts in a heart sound sensor signal.

FIG. 18 is a flow diagram illustrating an example method for rejecting motion artifacts in a heart sound sensor signal. The example method of FIG. 18 is described with respect to heart sound analyzer 80 and processor 70, but may be performed by any device, processor, or module described herein.

According to the example method of FIG. 18, processor 70 monitors the activity of patient 14, e.g., based on signals from an activity sensor 84, which may comprise one or more accelerometers (250). Processor 70 may also monitor the heart sound signal from heart sound sensor 82, and identify motion artifacts in the heart sound sensor signal that correspond to elements in the activity signal from sensor 84, e.g., that are time correlated with the elements in the activity signal (252). Processor 70 may reject the identified motion artifacts in the heart sound signal (254). For example, processor 70 may direct heart sound analyzer 80 to ignore or discard portions of the heart sound signal identified by processor 70 to be a motion artifact, or may ignore an indication regarding whether a cardiac rhythm is treatable or non-treatable from indication module 96 during a period of time corresponding to the motion artifact. In other examples, processor 70 may indicate the presence of a motion artifact to indication module 98, which may not apply the classification for one or more heart sounds that correspond in time to the motion artifact to a criterion, e.g., six of the last eight normal. In this manner, processor 70 may cause heart sound analyzer 80 to reject the motion artifact.

Figure 19:
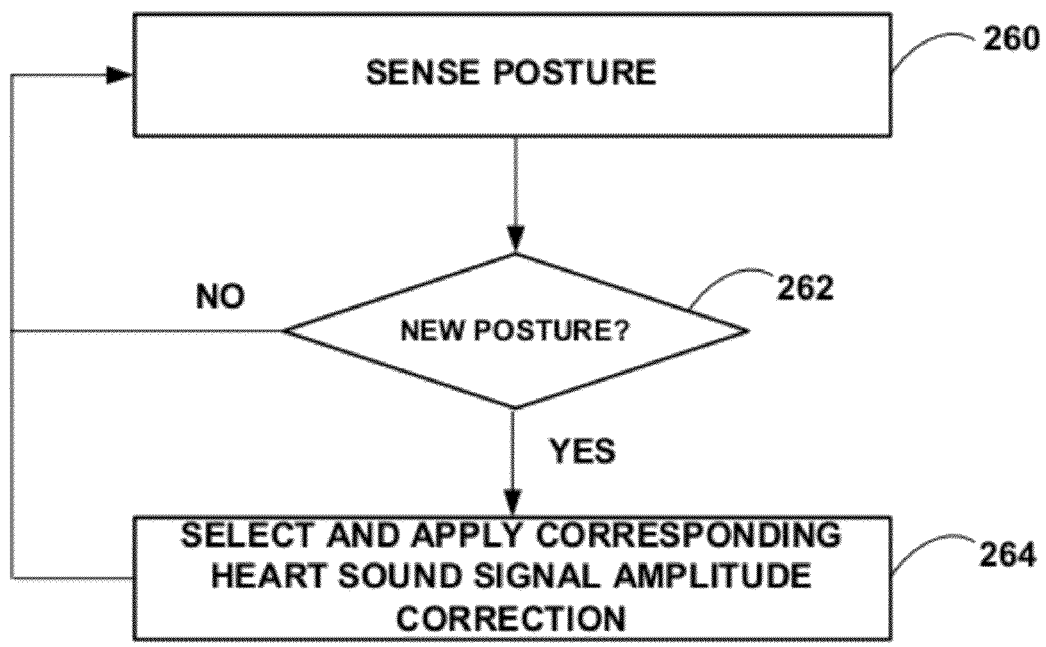
FIG. 19 is a flow diagram illustrating an example method for selecting a correction to a heart sound sensor signal amplitude based on posture.

FIG. 19 is a flow diagram illustrating an example method for selecting a correction to a heart sound sensor signal amplitude based on posture. The example method of FIG. 19 is described with respect to heart sound analyzer 80 and processor 70, but may be performed by any device, processor, or module described herein.

One or more of the amplitude and timing of the heart sound signal generated by heart sound sensor 82 may vary based on the posture of patient 14. This may be due to, for example, posture-dependent differences in the pressure within the thoracic cavity. For example, an increase in the thoracic pressure may increase the pressure required in the LV to overcome the pressure in the aorta which causes the aortic valve to open. The increased pressure may result in a larger amplitude heart sound and may delay the heart sound while the pressure builds in the LV. In order to compensate for these amplitude and/or timing differences and enable consistent detection of heart sounds despite these amplitude differences, memory 72 may store a table or other data structure that associates different postures (e.g., values or ranges of values of one or more signals from posture sensor 84) with different heart sound signal corrections. As an example, memory 72 may store data for adjusting the heart sound signal amplitude and data for adjusting a signal window relative to, for example, a sensed or paced cardiac depolarization.

Processor 70 senses posture of patient 14, e.g., based on signals from posture sensor 84, which may comprise one or more accelerometers (260). When processor 70 determines that patient 14 is in a new posture (262), processor 70 selects and applies a heart sound signal amplitude correction corresponding to the new posture (264). For example, processor 70 may adjust the initial value, after detection of a heart sound, of the adaptively decaying threshold applied by heart sound detector 92. The adjustment may be a numerical value for the threshold, a numerical value added or subtracted from the threshold, or a ratio, percentage or number by which the threshold is multiplied.

Figure 20:
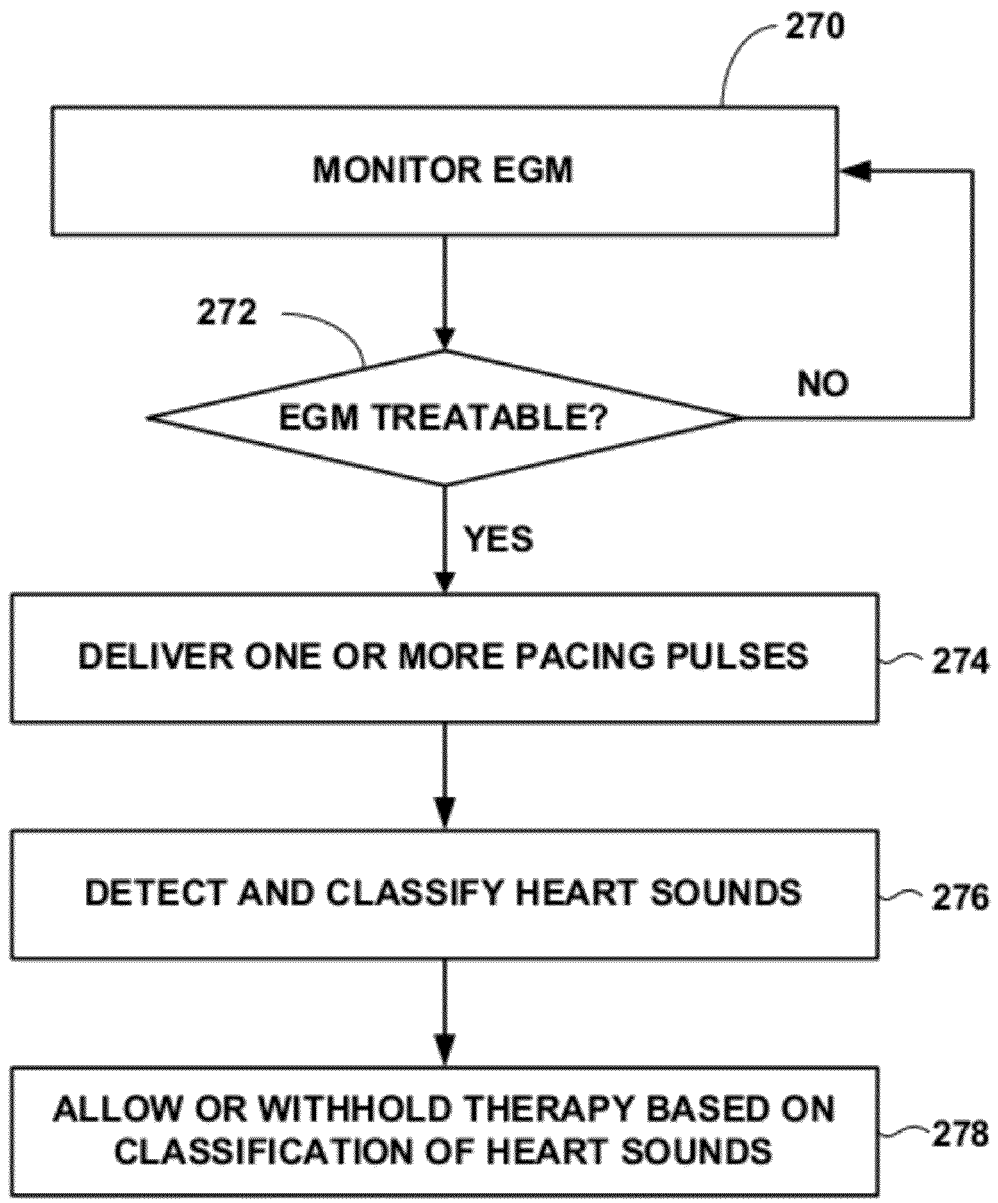
FIG. 20 is a flow diagram illustrating an example method for heart sound sensing during delivery of electrical pulses.

FIG. 20 is a flow diagram illustrating another example method for allowing or withholding a tachyarrhythmia therapy based on heart sound sensing. In some examples, the method illustrated in the flow diagram of FIG. 20 may also be used to determine the effectiveness of ATP therapy and, therefore, determine when to withhold or allow subsequent cardioversion or defibrillation therapy. The example method is described with respect to IMD 16 and its components shown in FIG. 3, but in other examples, may be practiced, at least in part, by another device, such as programmer 24.

According to the illustrated example, processor 70 monitors the EGM (270) and determines, based on the EGM (272), if the patient is experiencing a treatable cardiac rhythm, such as VF. If processor 70 determines that the rhythm is not a treatable rhythm, processor 70 continues to monitor the EGM (270). However, if processor 70 determines that the rhythm is treatable, processor 70 controls signal generator 74 to deliver one or more pacing pulses (274).

In some examples, processor 70 may cause signal generator 74 to deliver the pacing pulses as part of ATP. In such examples, processor 70 may cause signal generator 74 to deliver the pacing pulses during a confirmation phase of an arrhythmia detection algorithm, or before or during the charging of a capacitor for delivering cardioversion or defibrillation. Thus, the delivery of one or more pacing pulses (274) may occur prior to a decision that the rhythm is treatable based on an EGM analysis (272) in some examples.

Upon delivering the pacing pulses, processor 70 looks to heart sound analyzer 80 for an indication confirming that the heart rhythm is treatable. In some examples, heart sound analyzer 80 detects and classifies heart sounds as described herein (276) during the delivery of the pacing pulses. The presence of normal heart sounds may indicate the absence of fibrillation or another treatable tachyarrhythmia, and/or the success of ATP. Based on the classification of heart sounds during the delivery of the pacing pulses, processor 80 may allow or withhold a therapy, such as cardioversion or defibrillation (278).

Figure 21:
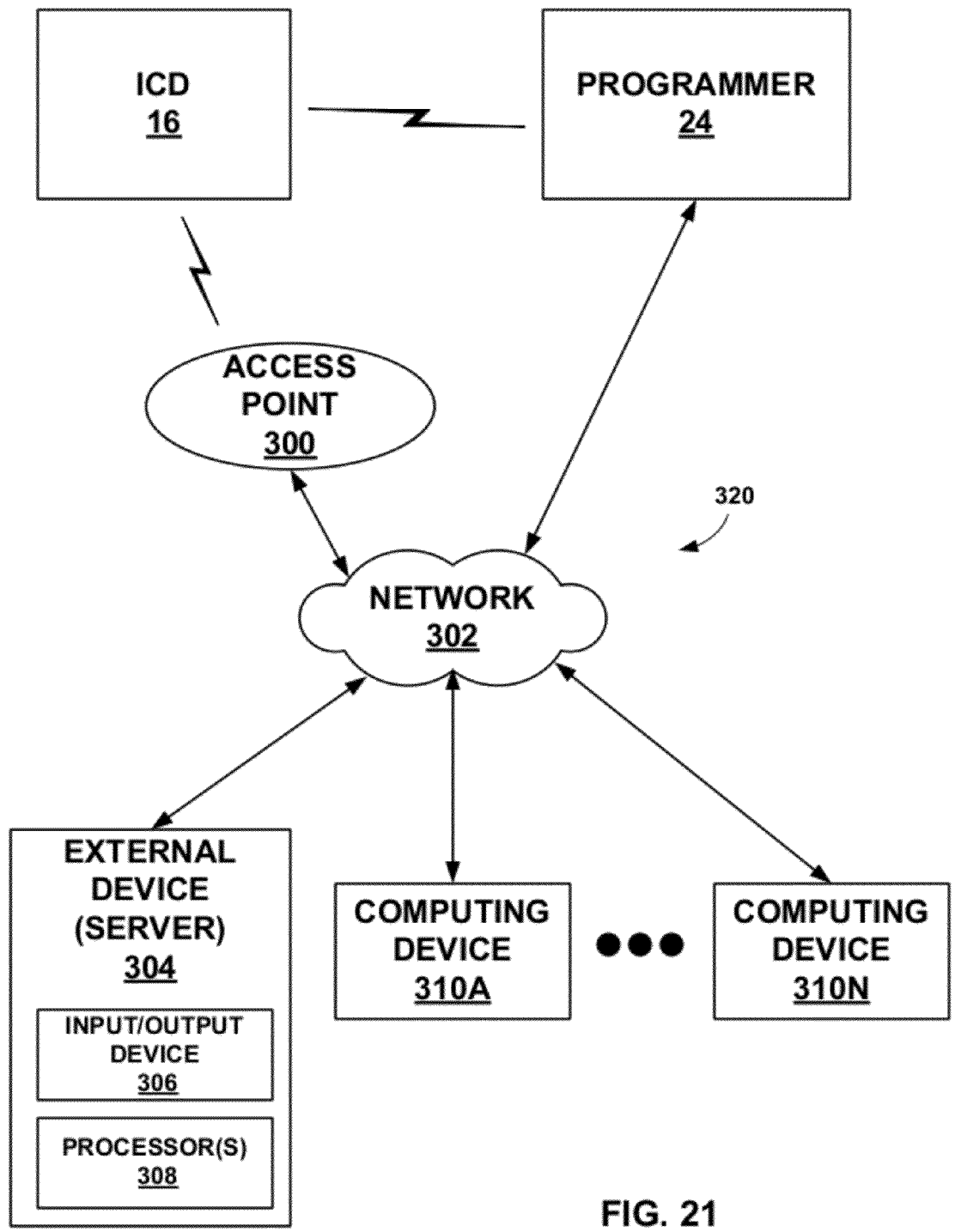
FIG. 21 illustrates an example system that includes an external device, such as a server, and one or more computing devices that are coupled to the IMD and programmer shown in FIG. 1 via a network.

FIG. 21 is a block diagram illustrating an example system 320 that includes an external device, such as a server 304, and one or more computing devices 310A-310N, that are coupled to the IMD 16 and programmer 24 shown in FIG. 1 via a network 302. In this example, IMD 16 may use its telemetry module 78 to communicate with programmer 24 via a first wireless connection, and to communication with an access point 300 via a second wireless connection. In the example of FIG. 21, access point 300, programmer 24, server 304, and computing devices 310A-310N are interconnected, and able to communicate with each other, through network 302. In some cases, one or more of access point 300, programmer 24, server 304, and computing devices 310A-310N may be coupled to network 302 through one or more wireless connections. IMD 16, programmer 24, server 304, and computing devices 310A-310N may each comprise one or more processors, such as one or more microprocessors, DSPs, ASICs, FPGAs, programmable logic circuitry, or the like, that may perform various functions and operations, such as those described herein. Network 302 may comprise a local area network, wide area network, or global network, such as the Internet. System 320 may be implemented, in some aspects, with general network technology and functionality similar to that provided by the Medtronic CareLink® Network developed by Medtronic, Inc., of Minneapolis, Minn.

Access point 300 may comprise a device that connects to network 302 via any of a variety of connections, such as telephone dial-up, digital subscriber line (DSL), or cable modem connections. In other embodiments, access point 300 may be coupled to network 302 through different forms of connections, including wired or wireless connections. In some embodiments, access point 300 may be co-located with a patient and may comprise one or more programming units and/or computing devices (e.g., one or more monitoring units) that may perform various functions and operations described herein. For example, access point 300 may include a home-monitoring unit that is co-located with the patient and that may monitor the activity of IMD 16.

In some examples, access point 300, server 304 or computing devices 310 may perform any of the various functions or operations described herein with respect to IMD 16 or programmer 24. For example, such devices may receive EGM, activity, posture, and/or heart sound signals from IMD 16 for analysis according to any of the techniques described herein.

Various examples have been described. These and other examples are within the scope of the following claims. For example, the techniques disclosed in this disclosure may be implemented by an implantable medical device that does not provide tachyarrhythmia therapies, such as an implantable monitoring device, an implantable pacemaker, or the like. In such examples, the techniques may provide for more accurate monitoring of a patient's heart rhythm. Moreover, although described primarily with reference to implantable medical devices, the techniques disclosed herein may be implemented by an external medical device, such as an external defibrillator, e.g., to improve tachyarrhythmia detection and reduce false shocks.

The techniques described in this disclosure, including those attributed to IMD 16, programmer 24, or various constituent components, may be implemented, at least in part, in hardware, software, firmware or any combination thereof. For example, various aspects of the techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic data storage media, optical data storage media, or the like. The instructions may be executed to support one or more aspects of the functionality described in this disclosure.

The invention claimed is:

1. A method comprising:
   determining that a cardiac rhythm of a heart of a patient is treatable by delivery of an antitachyarrhythmia therapy from a medical device to the patient based on an analysis of electrical activity of the heart of the patient;
   receiving a heart sound signal from a heart sound sensor, the heart sound signal representing sounds generated by the heart and bloodflow of the patient;
   detecting a plurality of heart sounds within the heart sound signal;
   classifying each of the detected heart sounds as one of a first classification or a second classification based on one or more features of the detected heart sounds;
   selectively delivering or withholding the antitachyarrhythmia therapy based on the classifications of the detected heart sounds; and
   generating an envelope signal of the heart sound signal, wherein detecting a plurality of heart sounds within the heart sound signal comprises detecting a plurality of heart sounds within the envelope signal, wherein generating the envelope signal comprises:
   bandpass filtering the heart sound signal;
   rectifying the filtered signal;
   smoothing the rectified signal; and
   applying a box-car filter to the smoothed signal to generate the envelope signal.

2. The method of claim 1, wherein the first classification comprises a normal classification and the second classification comprises an abnormal classification, and selectively delivering or withholding the antitachyarrhythmia therapy comprises withholding the tachyarrhythmia therapy if at least M of the last N detected heart sounds is classified as normal.

3. The method of claim 1, wherein the antitachyarrhythmia therapy comprises a defibrillation pulse.

4. The method of claim 1, wherein determining that the cardiac rhythm is treatable by delivery of the antitachyarrhythmia therapy from the medical device, receiving the heart sound signal, detecting the plurality of heart sounds, classifying each of the detected heart sounds, and selectively delivering or withholding the antitachyarrhythmia therapy comprises determining that the cardiac rhythm is treatable by delivery of the antitachyarrhythmia therapy, receiving the heart sound signal, detecting the plurality of heart sounds, classifying each of the detected heart sounds, and selectively delivering or withholding the antitachyarrhythmia therapy by the medical device.

5. The method of claim 4, wherein the medical device comprises an implantable cardiac device.

6. The method of claim 1, further comprising delivering a plurality of pacing pulses to the heart, wherein receiving the heart sound signal comprises receiving the heart sound signal during the delivery of the pacing pulses.

7. The method of claim 6, wherein delivering the plurality of pacing pulses comprises delivering antitachyarrhythmia pacing.

8. A method comprising:
   determining that a cardiac rhythm of a heart of a patient is treatable by delivery of an antitachyarrhythmia therapy from a medical device to the patient based on an analysis of electrical activity of the heart of the patient;
   receiving a heart sound signal from a heart sound sensor, the heart sound signal representing sounds generated by the heart and bloodflow of the patient;
   detecting a plurality of heart sounds within the heart sound signal;
   classifying each of the detected heart sounds as one of a first classification or a second classification based on one or more features of the detected heart sounds;
   selectively delivering or withholding the antitachyarrhythmia therapy based on the classifications of the detected heart sounds; and
   generating an envelope signal of the heart sound signal, wherein detecting a plurality of heart sounds within the heart sound signal comprises detecting a plurality of heart sounds within the envelope signal, and wherein detecting a plurality of heart sounds within the envelope signal comprises comparing the envelope signal to an adaptively decaying threshold to detect the heart sounds within the envelope signal.

9. The method of claim 8, wherein the adaptively decaying threshold decays at different rates during different heart sound intervals.

10. The method of claim 8, wherein the adaptively decaying threshold decays at a first decay rate during a first time interval after a most recently detected one of the heart sounds, and wherein the adaptively decaying threshold decays at a second decay rate that is greater than the first decay rate during a second time interval after the first time interval when one of the heart sounds is not detected during the first time interval.

11. The method of claim 8, further comprising:
stopping the decaying of the adaptively decaying threshold during a heart sound interval between consecutive detected heart sounds at a minimum value; and
maintaining the adaptively decaying threshold at the minimum value until detection of one of the heart sounds.

12. The method of claim 8, wherein an initial value for the adaptively decaying threshold after detection of one of the heart sounds comprises a running average of peak amplitude values of the envelope signal.

13. The method of claim 8, further comprising:
detecting a posture of the patient; and
determining an initial value for the adaptively decaying threshold after detection of one of the heart sounds based on the posture.

14. The method of claim 8, wherein detecting each of the plurality of heart sounds within the envelope signal comprises identifying a local maximum of the envelope signal when an amplitude of the envelope signal is greater than the adaptively decaying detection threshold.

15. The method of claim 14, wherein classifying each of the detected heart sounds as one of the first classification or the second classification based on the one or more features of the detected heart sounds comprises, for each of the detected heart sounds:
analyzing at least one of a segment of the envelope signal around the local maximum of the envelope signal for the heart sound or a segment of a filtered version of the heart sound signal around the local maximum of the envelope signal for the heart sound; and
determining the one or more features of the heart sound based on the analysis.

16. The method of claim 15, wherein analyzing the at least one of the segment of the envelope signal or the segment of the filtered version of the heart sound signal comprises comparing the at least one of the segments to at least one previously-collected template heart sound for the patient.

17. A system comprising:
a heart sound sensor that generates a heart sound signal representative of sounds generated by a heart and blood-flow of a patient;
a medical device;
a processor that determines that a cardiac rhythm of the heart is treatable by delivery of an antitachyarrhythmia therapy from the medical device to the patient based on an analysis of electrical activity of the heart of the patient; and
a heart sound analyzer that receives the heart sound signal from the heart sound sensor, detects a plurality of heart sounds within the heart sound signal, and classifies each of the detected heart sounds as one of a first classification or a second classification based on one or more features of the detected heart sounds, wherein the processor selectively controls the medical device to deliver or withhold the antitachyarrhythmia therapy based on the classifications of the detected heart sounds, wherein the heart sound analyzer comprises:
an envelope extractor configured to generate an envelope signal of the heart sound signal; and
a heart sound detector configured to detect the plurality of heart sounds within the envelope signal, and wherein the envelope extractor is configured to bandpass filter the heart sound signal, rectify the filtered signal, smooth the rectified signal, and apply a box-car filter to the smoothed signal to generate the envelope signal.

18. The system of claim 17, wherein the first classification comprises a normal classification and the second classification comprises an abnormal classification, and the processor controls the medical device to withhold the tachyarrhythmia therapy if at least M of the last N detected heart sounds is classified as normal.

19. The system of claim 17, wherein the antitachyarrhythmia therapy comprises a defibrillation pulse.

20. A system comprising:
a heart sound sensor that generates a heart sound signal representative of sounds generated by a heart and blood-flow of a patient;
a medical device;
a processor that determines that a cardiac rhythm of the heart is treatable by delivery of an antitachyarrhythmia therapy from the medical device to the patient based on an analysis of electrical activity of the heart of the patient; and
a heart sound analyzer that receives the heart sound signal from the heart sound sensor, detects a plurality of heart sounds within the heart sound signal, and classifies each of the detected heart sounds as one of a first classification or a second classification based on one or more features of the detected heart sounds,
wherein the processor selectively controls the medical device to deliver or withhold the antitachyarrhythmia therapy based on the classifications of the detected heart sounds, wherein the heart sound analyzer comprises:
an envelope extractor configured to generate an envelope signal of the heart sound signal; and
a heart sound detector configured to detect the plurality of heart sounds within the envelope signal, wherein the heart sound detector compares the envelope signal to an adaptively decaying threshold to detect the heart sounds within the envelope signal.

21. The system of claim 20, wherein the heart sound detector decays the adaptively decaying threshold at different rates during different heart sound intervals.

22. The system of claim 20, wherein the heart sound detector decays the adaptively decaying threshold at a first decay rate during a first time interval after a most recently detected one of the heart sounds, and wherein the heart sound detector decays the adaptively decaying threshold at a second decay rate that is greater than the first decay rate during a second time interval after the first time interval when one of the heart sounds is not detected during the first time interval.

23. The system of claim 20, wherein the heart sound detector stops the decaying of the adaptively decaying threshold during a heart sound interval between consecutive detected heart sounds at a minimum value, and maintains the adaptively decaying threshold at the minimum value until detection of one of the heart sounds.

24. The system of claim 20, wherein an initial value for the adaptively decaying threshold after detection of one of the heart sounds comprises a running average of peak amplitude values of the envelope signal.

25. The system of claim 20, wherein the processor detects a posture of the patient, and determines an initial value for the adaptively decaying threshold after detection of one of the heart sounds based on the posture.

26. The system of claim 20, wherein the heart sound detector is configured to identify local maxima of the envelope signal when an amplitude of the envelope signal is greater than the adaptively decaying detection threshold as the heart sounds.

27. The system of claim 26, wherein the heart sound analyzer further comprises a heart sound feature module configured to analyze at least one of a segment of the envelope signal around the local maximum of the envelope signal for the heart sound or a segment of a filtered version of the heart sound signal around the local maximum of the envelope signal for the heart sound, and determine the one or more features of the heart sound based on the analysis.

28. The system of claim 27, wherein the heart sound feature module is configured to compare the at least one of the segments to at least one previously-collected template heart sound for the patient.

29. The system of claim 17, wherein the medical device comprises an implantable cardiac device that comprises the processor and comprises or is coupled to the heart sound sensor.

30. The system of claim 17, further comprising a signal generator, wherein the processor controls the signal generator to deliver a plurality of pacing pulses to the heart, and the heart sound analyzer receives the heart sound signal during the delivery of the pacing pulses.

31. The system of claim 30, wherein the processor controls the signal generator to deliver antitachyarrhythmia pacing, and the heart sound analyzer receives the heart sound signal during the delivery of the antitachyarrhythmia pacing.

32. A system comprising:
- means for determining that a cardiac rhythm of a heart of a patient is treatable by delivery of an antitachyarrhythmia therapy from a medical device to the patient based on an analysis of electrical activity of the heart of the patient;
- means for receiving a heart sound signal from a heart sound sensor, the heart sound signal representing sounds generated by the heart and bloodflow of the patient;
- means for detecting a plurality of heart sounds within the heart sound signal;
- means for classifying each of the detected heart sounds as one of a first classification or a second classification based on one or more features of the detected heart sounds; and
- means for selectively delivering or withholding the antitachyarrhythmia therapy based on the classifications of the detected heart sounds, wherein the means for detecting a plurality of heart sounds within the envelope signal comprises means for comparing the envelope signal to an adaptively decaying threshold to detect the heart sounds within the envelope signal.

33. The system of claim 32, further comprising means for generating an envelope signal of the heart sound signal, wherein the means for detecting the plurality of heart sounds within the heart sound signal comprises means for detecting the plurality of heart sounds within the envelope signal.

* * * * *